United States Patent
Nakano et al.

(10) Patent No.: US 10,801,058 B2
(45) Date of Patent: Oct. 13, 2020

(54) METHOD OF QUALITY CONTROL OF NUCLEIC ACID AMPLIFICATION

(71) Applicant: SYSMEX CORPORATION, Kobe-shi, Hyogo (JP)

(72) Inventors: Tsuyoshi Nakano, Kobe (JP); Yuichiro Yoshida, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 398 days.

(21) Appl. No.: 15/405,684

(22) Filed: Jan. 13, 2017

(65) Prior Publication Data

US 2017/0211138 A1  Jul. 27, 2017

(30) Foreign Application Priority Data

Jan. 27, 2016 (JP) ................................. 2016-013692

(51) Int. Cl.
- C12Q 1/68 (2018.01)
- C12Q 1/6851 (2018.01)
- C12Q 1/6853 (2018.01)

(52) U.S. Cl.
CPC ......... *C12Q 1/6851* (2013.01); *C12Q 1/6853* (2013.01)

(58) Field of Classification Search
None
See application file for complete search history.

(56) References Cited

U.S. PATENT DOCUMENTS

| | | | |
|---|---|---|---|
| 2001/0006800 A1* | 7/2001 | Walkerpeach | C12Q 1/6851 435/91.1 |
| 2008/0096213 A1 | 4/2008 | Kajita et al. | |
| 2009/0143233 A1 | 6/2009 | Knight et al. | |
| 2010/0041048 A1 | 2/2010 | Diehl et al. | |
| 2014/0236496 A1 | 8/2014 | Janaway et al. | |
| 2015/0133319 A1 | 5/2015 | Fu et al. | |

FOREIGN PATENT DOCUMENTS

| | | |
|---|---|---|
| JP | 2008-72950 A | 4/2008 |
| JP | 2010-524430 A | 7/2010 |
| JP | 2014-534497 A | 12/2014 |
| JP | 2015-511819 A | 4/2015 |
| WO | 2014145467 A2 | 9/2014 |
| WO | 2014145467 A3 | 9/2014 |
| WO | 2014172373 A2 | 10/2014 |
| WO | 2014172373 A3 | 10/2014 |
| WO | 2015143385 A1 | 9/2015 |

OTHER PUBLICATIONS

Akbarian A, Shahhosseiny MH, Vafaei S, Moslemi E, Ghahri M. Designing novel and simple competitive internal amplification control for reliable PCR diagnosis of herpes simplex virus. Jundishapur J Microbiol. Feb. 20, 2015; 8(2):e16260. Epub. Feb. 2015. (Year: 2015).*

Burggraf S, Olgemöller B. Simple technique for internal control of real-time amplification assays. Clin Chem. May 2004; 50(5):819-25. Epub Mar. 9, 2004. (Year: 2004).*

Hoorfar J, Malorny B, Abdulmawjood A, Cook N, Wagner M, Fach P. Practical considerations in design of internal amplification controls for diagnostic PCR assays. J Clin Microbiol. May 2004; 42(5):1863-8. (Year: 2004).*

Stocher M, Leb V, Berg J. A convenient approach to the generation of multiple internal control DNA for a panel of real-time PCR assays. J Virol Methods. 2003; 108(1):1-8. (Year: 2003).*

Frank Diehl et al., "BEAMing: single-molecule PCR on microparticles in water-in-oil emulsions", Nature Methods, Jul. 2006, pp. 551-559, vol. 3, No. 7.

Luis A. Diaz Jr., et al., "The molecular evolution of acquired resistance to targeted EGFR blockade in colorectal cancers", Nature, Jun. 28, 2012, pp. 537-540, vol. 486 with Supplemental Information.

Nele Wellinghausen et al., "Detection of Legionellae in Hospital Water Samples by Quantitative Real-Time LightCycler PCR", Applied and Environmental Microbiology, Sep. 2001, pp. 3985-3993, vol. 67, No. 9.

Japanese Office Action dated Oct. 23, 2019 in a counterpart Japanese patent application No. 2016-013692.

* cited by examiner

Primary Examiner — Gary Benzion
Assistant Examiner — Olayinka A Oyeyemi
(74) Attorney, Agent, or Firm — Sughrue Mion PLLC

(57) ABSTRACT

Disclosed is a method of quality control of nucleic acid amplification using quality control oligonucleotide. The method comprises a nucleic acid detection step and a determination step. The nucleic acid detection step comprises the steps of: preparing a nucleic acid sample containing a target nucleic acid and a quality control polynucleotide; preparing a compartment containing one molecule of the target nucleic acid and a compartment containing one molecule of the quality control polynucleotide; and carrying out nucleic acid amplification of the target nucleic acid and the quality control polynucleotide, in the compartments, and carrying out signal detection using a detection probe to detect a signal originated from the detection probe. In the determination step, it is determined as to whether or not the nucleic acid detection step is proper on the basis of the result obtained in the signal detection step.

19 Claims, 11 Drawing Sheets
Specification includes a Sequence Listing.

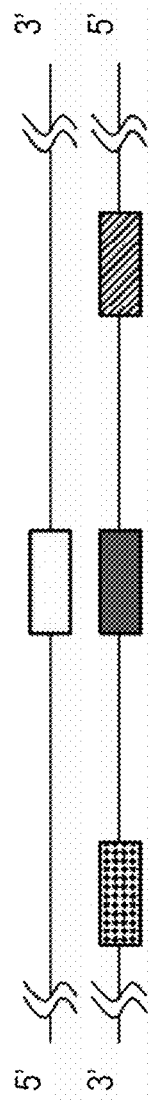
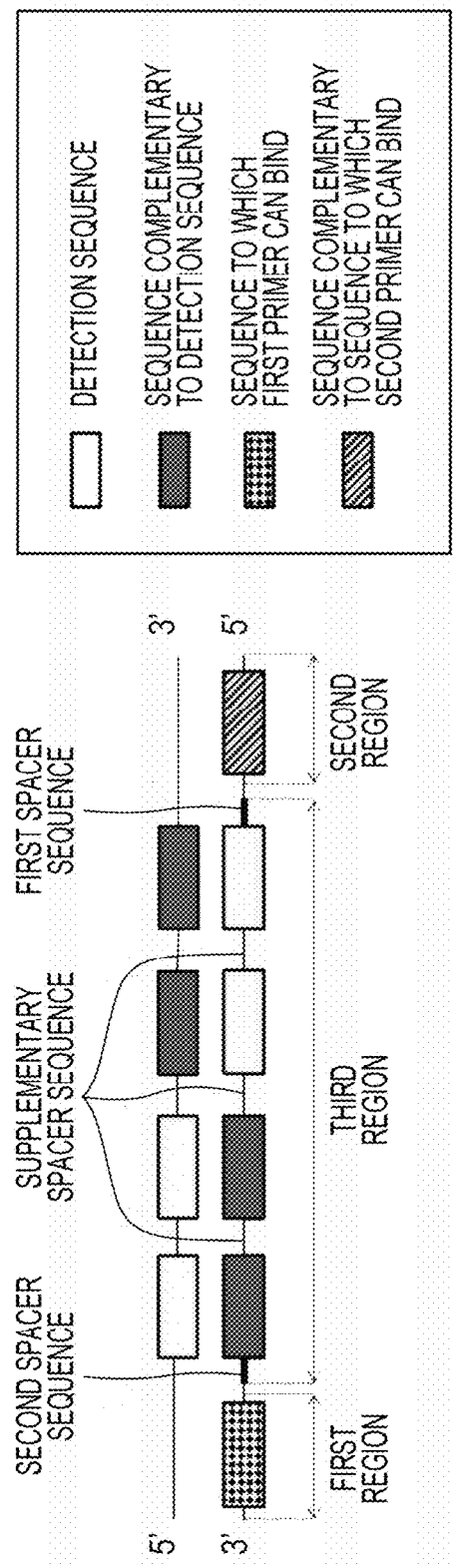

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer
```

<400> SEQUENCE: 1
tcccgcgaaa ttaatacgac                                                          20

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 2
gctggagctc tgcagcta                                                            18

<210> SEQ ID NO 3
<211> LENGTH: 45
<212> TYPE: DNA
<213> ORGANISM: Artificial Sequence
<220> FEATURE:
<223> OTHER INFORMATION: Synthetic oligonucleotide primer

<400> SEQUENCE: 3
gctggagctc tgcagctatg actgaatata aacttgtggt agttg                              45

<210> SEQ ID NO 4
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 4
tcccgcgaaa ttaatacgac catattcgtc cacaaaatga ttc                                43

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide probe

<400> SEQUENCE: 5
tgacgataca gctaattca                                                           19

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide probe

<400> SEQUENCE: 6
tgctggtggc gtaggc                                                              16

<210> SEQ ID NO 7
<211> LENGTH: 16
<212> TYPE: DNA
<213> ORGANISM: Artificial Sequence
<220> FEATURE:
<223> OTHER INFORMATION: Synthetic oligonucleotide probe

<400> SEQUENCE: 7
tgctggtgac gtaggc                                                              16

<210> SEQ ID NO 8

<211> LENGTH: 122
<212> TYPE: DNA
<213> ORGANISM: Homo sapiens

<400> SEQUENCE: 8
ctctattgtt ggatcatatt cgtccacaaa atgattctga attagctgta tcgtcaaggc    60
actcttgcct acgccaccag ctccaactac cacaagttta tattcagtca ttttcagcag    120
gc    122

<210> SEQ ID NO 9
<211> LENGTH: 122
<212> TYPE: DNA
<213> ORGANISM: Homo sapiens

<400> SEQUENCE: 9
ctctattgtt ggatcatatt cgtccacaaa atgattctga attagctgta tcgtcaaggc    60
actcttgcct acgtcaccag ctccaactac cacaagttta tattcagtca ttttcagcag    120
gc    122

<210> SEQ ID NO 10
<211> LENGTH: 158
<212> TYPE: DNA
<213> ORGANISM: Artificial Sequence
<220> FEATURE:
<223> OTHER INFORMATION: Synthetic tandem DNA, n=5 (OBQ_R050-04)

<400> SEQUENCE: 10
tcatattcgt ccacaaaatg attcagatgc ctacgccacc agctatcagc ctacgccacc    60
agctcagtgc ctacgccacc agctactagc ctacgccacc agctatgagc ctacgccacc    120
agctacgatg caactaccac aagtttatat tcagtcat    158

<210> SEQ ID NO 11
<211> LENGTH: 158
<212> TYPE: DNA
<213> ORGANISM: Artificial Sequence
<220> FEATURE:
<223> OTHER INFORMATION: Synthetic tandem DNA, n=4 (OBQ_R040-11)

<400> SEQUENCE: 11
tcatattcgt ccacaaaatg attcagatgc ctacgccacc agctatcagc ctacgccacc    60
agctcagtgc ctacgccacc agctactagc ctacgccacc agctatgaac ctctattgtt    120
ggatacgatg caactaccac aagtttatat tcagtcat    158

<210> SEQ ID NO 12
<211> LENGTH: 158
<212> TYPE: DNA
<213> ORGANISM: Artificial Sequence
<220> FEATURE:
<223> OTHER INFORMATION: Synthetic tandem DNA, n=3 (OBQ_R030-12)

<400> SEQUENCE: 12
tcatattcgt ccacaaaatg attcagatgc ctacgccacc agctatcagc ctacgccacc    60
agctcagtgc ctacgccacc agctactata ttaaaacaag atttatgaac ctctattgtt    120
ggatacgatg caactaccac aagtttatat tcagtcat    158

<210> SEQ ID NO 13
<211> LENGTH: 158
<212> TYPE: DNA
<213> ORGANISM: Artificial Sequence

```
<220> FEATURE:
<223> OTHER INFORMATION: Synthetic tandem DNA, n=2 (OBQ_R020-13)

<400> SEQUENCE: 13
tcatattcgt ccacaaaatg attcagatgc ctacgccacc agctatcagc ctacgccacc        60
agctcagtgc accagtaata tgcaactata ttaaaacaag atttatgaac ctctattgtt       120
ggatacgatg caactaccac aagtttatat tcagtcat                                158

<210> SEQ ID NO 14
<211> LENGTH: 150
<212> TYPE: DNA
<213> ORGANISM: Artificial Sequence
<220> FEATURE:
<223> OTHER INFORMATION: Synthetic tandem DNA, n=5, mut-form
      (OBQ_R005-03)

<400> SEQUENCE: 14
tcatattcgt ccacaaaatg attctgccta cgtcaccagc tatcagccta cgtcaccagc        60
tcagtgccta cgtcaccagc tactagccta cgtcaccagc tatgagccta cgtcaccagc       120
tccaactacc acaagtttat attcagtcat                                         150

<210> SEQ ID NO 15
<211> LENGTH: 155
<212> TYPE: DNA
<213> ORGANISM: Artificial Sequence
<220> FEATURE:
<223> OTHER INFORMATION: Synthetic tandem DNA, n=6 (OBQ_R060-01)

<400> SEQUENCE: 15
tcatattcgt ccacaaaatg attctgccta cgccaccagc tagcctacgc caccagcttg        60
cctacgccac cagctggcct acgccaccag ctcgcctacg ccaccagcta gcctacgcca       120
ccagctccaa ctaccacaag tttatattca gtcat                                   155
```

METHOD OF QUALITY CONTROL OF NUCLEIC ACID AMPLIFICATION

CROSS REFERENCE TO RELATED APPLICATIONS

This application claims priority from prior Japanese Patent Application No. 2016-013692, filed on Jan. 27, 2016, entitled "METHOD FOR CONTROLLING QUALITY OF NUCLEIC ACID AMPLIFICATION, REAGENT FOR USE IN QUALITY CONTROL, AND REAGENT KIT INCLUDING SAID REAGENT", the entire contents of which are incorporated herein by reference.

TECHNICAL FIELD

The present invention relates to a method for controlling quality of nucleic acid amplification.

BACKGROUND

In a nucleic acid amplification method, there may be cases where a proper result cannot be obtained due to various factors including amplification errors caused by a polymerase, inhibition of amplification by contaminants or the like and incorrect operation during the preparation of samples. Therefore, it is needed to control the quality whether or not the amplification of a nucleic acid is performed properly.

Appl. Environ. Mocrobiol. 2001. 67, 3985-3993 discloses a control polynucleotide which has: a region to which a primer set that is the same as that for a target nucleic acid can bind; and a region to which a probe that is different from a detection probe for detecting the target nucleic acid can bind. The detection probe for detecting the target nucleic acid and a probe for detecting the control polynucleotide are labeled with different fluorescent dyes from each other. Thus, an amplification product of the target nucleic acid and an amplification product of the control polynucleotide can be detected separately and simultaneously in a single reaction vessel (p. 3986, the section "Primes, Probes, and PCR assay" in the right column, and p. 3990, FIG. 2).

In recent years, a digital nucleic acid detection method has been developed as a method for detecting a nucleic acid molecule to be targeted (also referred to as a "target nucleic acid", hereinafter) in a sample. More specifically, the digital nucleic acid detection method is a method in which one molecule of a target nucleic acid is placed in each of separated zones (also simply referred to as "compartments", hereinafter) such as microwells and droplets and subsequently nucleic acid amplification is carried out in each of the compartments to detect the target nucleic acid with high sensitivity. The method disclosed in Non-Patent Document 1 appears to be applied to the digital nucleic acid detection method. In the method, however, different probes are used for a target nucleic acid and a control polynucleotide and therefore it is difficult to determine whether or not the probe for detecting the target nucleic acid acts correctly.

SUMMARY OF THE INVENTION

The scope of the present invention is defined solely by the appended claims, and is not affected to any degree by the statements within this summary.

The present inventors have accomplished a quality control method that can be used suitably for digital nucleic acid detection. That is, the present inventors have found that the control of quality can be achieved by using an oligonucleotide which has different number of regions to each of which a target nucleic acid detection probe can bind from the number of target nucleic acids between a region to which the same primer set as that for the target nucleic acid can bind and a region to which the primer set can bind in digital nucleic acid detection.

The present invention relates to a method for controlling quality of nucleic acid amplification, a reagent for use in quality control and a reagent kit for use in the quality control.

The present invention provides a method of quality control of nucleic acid amplification, comprising a nucleic acid detection step and a determination step. The nucleic acid detection step comprises the steps of: preparing a nucleic acid sample containing a target nucleic acid and a quality control polynucleotide; preparing a compartment containing one molecule of the target nucleic acid and a compartment containing one molecule of the quality control polynucleotide; and carrying out nucleic acid amplification of the target nucleic acid and the quality control polynucleotide, in the compartments, and carrying out signal detection using a detection probe to detect a signal originated from the detection probe. In the determination step, it is determined as to whether or not the nucleic acid detection step is proper on the basis of the result obtained in the signal detection step. In the method, the target nucleic acid contains a detection sequence. In the method, the quality control polynucleotide is (1) a single-stranded polynucleotide which contains a first region, a second region and a third region, wherein the first region contains a sequence to which a first primer for target nucleic acid amplification can bind, the second region contains a sequence complementary to a sequence to which a second primer for target nucleic acid amplification can bind, and the third region contains one or both of the detection sequence and a sequence complementary to the detection sequence, (2) a single-stranded polynucleotide which contains a sequence complementary to the sequence recited in item (1), or (3) a double-stranded polynucleotide which contains both the polynucleotide recited in item (2) and the polynucleotide recited in item (2). The detection probe contains a sequence complementary to the detection sequence. The total number of the detection sequence and complementary sequence to the detection sequence in the quality control polynucleotide recited in item (1) is different from the number of the detection sequence in the target nucleic acid.

BRIEF DESCRIPTION OF THE DRAWINGS

In FIG. 6A, a quality control polynucleotide (Mut, n=5) is present (+). In FIG. 6B, the quality control polynucleotide (Mut, n=5) is absent (−). In each of FIGS. 6A and 6B, a signal that reflects an amplification product of a mutant (Mut) KRAS gene is assigned to x-axis and a signal that reflects an amplification product of a wild-type (Wt) KRAS gene is assigned to y-axis;

In FIG. 9A, a quality control polynucleotide (Wt, n=6) is present (+). In FIG. 9B, the quality control polynucleotide (Wt, n=6) is absent (−). In each of FIGS. 9A and 9B, a signal that reflects an amplification product of a mutant (Mut) KRAS gene is assigned to x-axis and a signal that reflects an amplification product of a wild-type (Wt) KRAS gene is assigned to y-axis;

FIGS. 11A and 11B show schematic diagrams respectively illustrating a target nucleic acid and a quality control polynucleotide according to one embodiment.

DETAILED DESCRIPTION OF THE PREFERRED EMBODIMENTS

[Quality Control Method]

Figure 1:
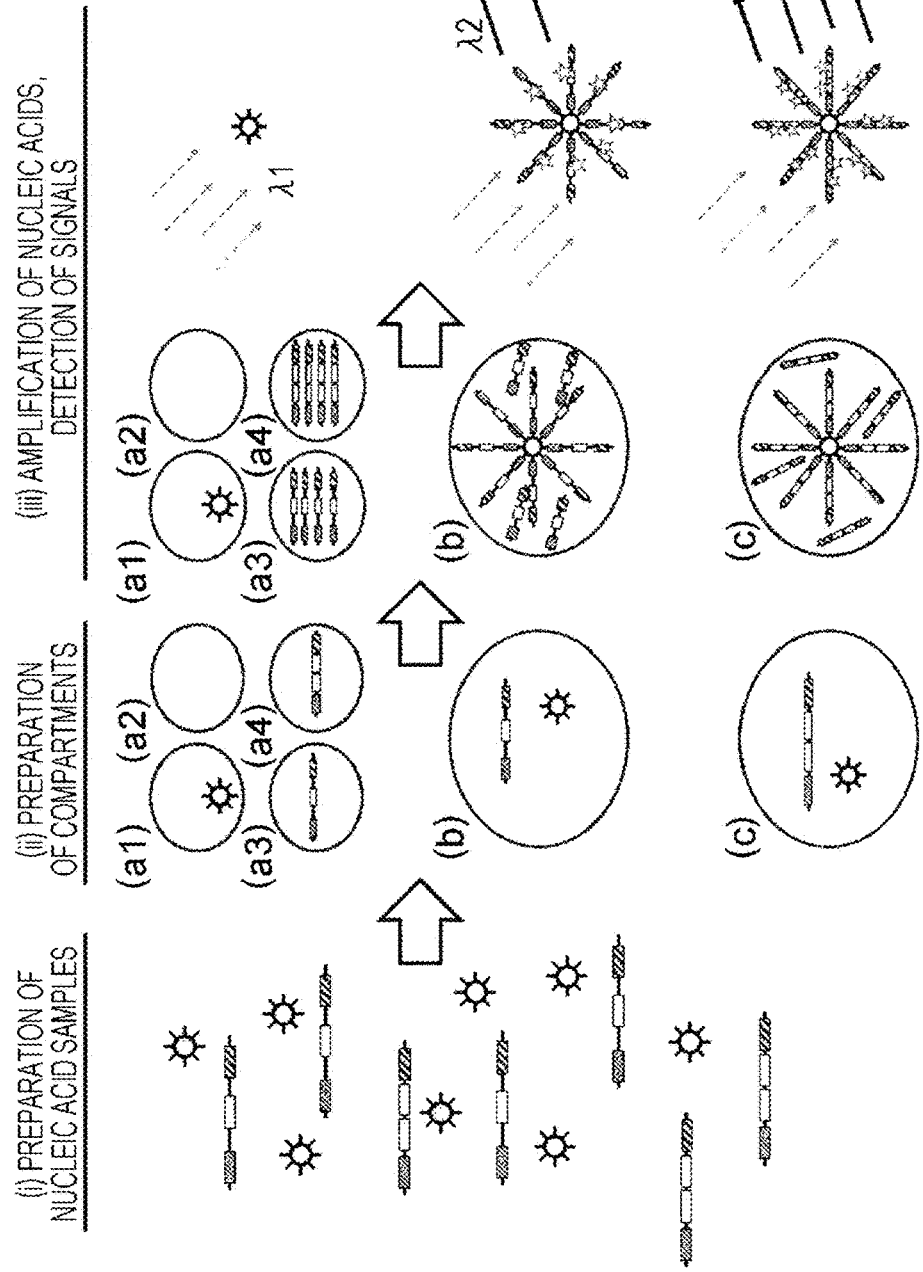
FIG. 1 shows a schematic diagram illustrating the nucleic acid detection step in Embodiment 1.

The first aspect relates to a method for controlling quality of nucleic acid amplification, which includes a nucleic acid detection step and a determination step. In the nucleic acid detection step in the first aspect, a nucleic acid sample containing a target nucleic acid and a quality control polynucleotide (i.e., polynucleotide for quality control purposes) is prepared. In one embodiment, this nucleic acid sample preparation step includes preparing a nucleic acid sample by mixing a sample containing the target nucleic acid with a sample containing the quality control polynucleotide.

The term "nucleic acid" as used herein refers to DNA or RNA. The nucleic acid is not limited particularly as long as the nucleic acid can be amplified, and a nucleotide derivative may form a part or the whole area of the nucleic acid. Examples of the nucleotide derivatives include a locked nucleic acid (LNA) and a bridged nucleic acid (BNA).

The term "nucleic acid sample" is not limited particularly, as long as the nucleic acid sample contains a nucleic acid. Examples of the nucleic acid sample include a biological sample such as blood and a lymphocyte, an excretion material such as urine and feces, and an environmental sample such as river water, sea water and soil. The nucleic acid sample generally has a liquid form. In the case where the sample is not in a liquid form, it is preferred to subject the sample to an appropriate pretreatment to make the sample into a liquid form. The "liquid" sample is not limited to a solution in which a solute is completely dissolved, and may be a suspension in which fine solid matters such as cells or cell debris are suspended or a sol. As the method of the pretreatment, any known method can be selected appropriately. For example, in the case where the sample is a tissue collected from a living body, the nucleic acid sample can be prepared by disrupting cells in the tissue in a pretreatment solution and then separating/removing debris from the solution by centrifugation or the like.

The term "target nucleic acid" as used herein has a sequence of interest (also refers to "a detection sequence" or "a sequence to be detected", hereinafter). Examples of the target nucleic acid include a nucleic acid contained in the nucleic acid sample, as well as an amplification product (amplicon) produced by amplifying DNA or RNA contained in the nucleic acid sample, and cDNA synthesized from RNA in the nucleic acid sample by a reverse transcription reaction. The target nucleic acid is generally originated from an organism or a virus.

The quality control polynucleotide according to the present disclosure can be amplified with the same primer as a primer capable of amplifying a region that contains the detection sequence in the target nucleic acid (wherein the primer is also referred to as "a target nucleic acid amplification primer" or "a primer for target nucleic acid amplification purposes, hereinafter). A target nucleic acid amplification primer set (i.e., a primer set for target nucleic acid amplification purposes) includes a first target nucleic acid amplification primer (also referred to as a "first primer", hereinafter) and a second target nucleic acid amplification primer (also referred to as a "second primer", hereinafter). In the quality control polynucleotide, a region containing a sequence to which the first primer can bind is referred to as a first region, and a region containing a sequence complementary to a sequence to which the second primer can bind is referred to as a second region.

In a region in the quality control polynucleotide which is to be amplified with the target nucleic acid amplification primer, one or both of the detection sequence and a sequence complementary to the detection sequence are contained. In the quality control polynucleotide, the region containing one or both of the detection sequence and a sequence complementary to the detection sequence is referred to as a third region.

The total number of detection sequences and sequences complementary to the detection sequences in the third region of the quality control polynucleotide is different from the number of detection sequences in a region of the target nucleic acid which is to be amplified with the target nucleic acid amplification primer. This means that the number of detection probes capable of hybridizing with an amplification product of the quality control polynucleotide is different from the number of detection probes capable of hybridizing with an amplification product of the target nucleic acid. This also means that, for example, the intensity of a detection probe-originated signal coming from a compartment or bead containing an amplification product of the quality control polynucleotide is different from the intensity of a detection probe-originated signal coming from a compartment or bead containing an amplification product of the target nucleic acid. With utilizing these differences, a compartment or bead containing an amplification product of the quality control polynucleotide can be distinguished from a compartment or bead containing an amplification product of the target nucleic acid.

In the case where the total number of detection sequences and sequences complementary to the detection sequences in the quality control polynucleotide, which is a single-stranded polynucleotide containing the first region, the second region and the third region, is larger than the number of detection sequences in the target nucleic acid, a compartment or bead containing an amplification product of the quality control polynucleotide generates a more intense signal than a compartment or bead containing an amplification product of the target nucleic acid. In the case where the number of detection sequences in the target nucleic acid is larger than the total number of detection sequences and sequences complementary to the detection sequences in the quality control polynucleotide, on the other hand, a compartment or bead containing an amplification product of the target nucleic acid generates a more intense signal than a compartment or bead containing an amplification product of the quality control polynucleotide. Hereinafter, the wording "the total number of detection sequences and sequences complementary to the detection sequences" refers to the total number of detection sequences and sequences complementary to detection sequences in the quality control polynucleotide which is a single-stranded polynucleotide containing the first region, the second region and the third region.

The total number of detection sequences and sequences complementary to the detection sequences in the quality control polynucleotide is, but is not limited to, preferably at least one larger than the number of detection sequences in the target nucleic acid. In general, the number of detection sequences in the target nucleic acid is 1. Therefore, the total number of detection sequences and sequences complementary to the detection sequences in a quality control polynucleotide can be set to 2 or more.

The total number of detection sequences and sequences complementary to the detection sequences in the quality control polynucleotide may be, but is not limited to, 20 or less, 10 or less, preferably 6 or less. The number may be, for example, 1 to 10 inclusive, 2 to 10 inclusive, or 2 to 6 inclusive. The quality control polynucleotide has, but not limited to, at least two detection sequences.

The quality control polynucleotide may be in a single-stranded form or a double-stranded form. A single-stranded polynucleotide has the advantage of being produced easily, at low cost and with high purity. A double-stranded polynucleotide can exert a tendency of being physically stable compared with a single-stranded polynucleotide. The quality control polynucleotide may be provided in a single-stranded form or a double-stranded form depending on the intended use.

The chain length of the quality control polynucleotide may be, but is not limited to, 1000 bp or less, 500 bp or less or 200 bp or less, from the viewpoint of easiness of the preparation of the quality control polynucleotide. In one embodiment, the chain length of the quality control polynucleotide is 50 to 200 bp inclusive, 80 to 170 bp inclusive, more preferably 90 to 160 bp inclusive. The difference between the chain length of the quality control polynucleotide and the chain length of an amplification product of the target nucleic acid is preferably set to, for example, a value falling within such a range that the levels of amplification efficiency of the quality control polynucleotide and the amplification product can become the same as each other in the nucleic acid amplification.

In one embodiment, the quality control polynucleotide contains a first spacer sequence upstream from the third region and a second spacer sequence downstream from the third region. In one embodiment, the first spacer sequence and the second spacer sequence are different from each other, and the first spacer sequence and the second spacer sequence are not complementary to each other. The wording "the first spacer sequence and the second spacer sequence are different from each other" means that a sequence completely complementary to one of the spacer sequences cannot hybridize with the other of the spacer sequences under stringent conditions. The wording "the first spacer sequence and the second spacer sequence are not complementary to each other" means that these sequences cannot hybridize with each other under stringent conditions.

In the case where the total number of detection sequences and sequences complementary to the detection sequences in the quality control polynucleotide is 2 or more, the quality control polynucleotide also contains a supplementary spacer sequence, for example, between one detection sequence and another detection sequence. The term "a supplementary spacer sequence" refers to a sequence which is different from the first spacer sequence and the second spacer sequence and is not complementary to each of the first spacer sequence and the second spacer sequence. With respect to the supplementary spacer sequence, the wordings "sequences are different from each other" and "sequences are not complementary to each other" have the same meanings as those which are mentioned with respect to the first spacer sequence and the second spacer sequence. The number of supplementary spacer sequences can be increased or decreased depending on the total number of detection sequences and sequences complementary to the detection sequences in the third region in the quality control polynucleotide. The wordings "sequences are different from each other" and "sequences are complementary to each other" which are mentioned with respect to the term "supplementary spacer sequence" can apply to the relation between supplementary spacer sequences.

In the case where the spacer sequences are identical or complementary to each other, there is a possibility that the hybridization between a spacer sequence and a strand complementary to the spacer sequence or the hybridization between spacer sequences occurs particularly in the latter stage of the nucleic acid amplification reaction. For decreasing this possibility, it is preferred that the first spacer sequence and the second spacer sequence are different from each other and the first spacer sequence and the second spacer sequence are not complementary to each other. This matter can apply to the supplementary spacer sequence.

In one embodiment, the length of the spacer sequence may be, for example, 1 to 20 bp inclusive, 1 to 10 bp inclusive, 2 to 10 bp inclusive, 3 to 10 bp inclusive, or 4 to 10 bp inclusive.

For illustrative purposes, the schematic diagrams respectively illustrating a quality control polynucleotide and a target nucleic acid according to one embodiment are shown in FIG. 11. FIG. 11A shows a target nucleic acid in which the number of detection sequences in a region to be amplified is 1. FIG. 11B shows a double-stranded quality control polynucleotide, in which the total number of detection sequences and sequences complementary to the detection sequences in the quality control polynucleotide is 4. More specifically, the quality control polynucleotide is composed of: a polynucleotide which contains a first region containing a sequence to which a first primer can bind, a second region containing a sequence complementary to a sequence to which a second primer can bind, and a third region containing two detection sequences and two sequences complementary to the detection sequences; and a polynucleotide which contains a sequence complementary to the sequence for the aforementioned polynucleotide. The third region contains a first spacer sequence upstream from the third region and a second spacer sequence downstream from the third region. In the third region, the total number of detection sequences and sequences complementary to the detection sequences is 2 or more, and therefore supplementary spacer sequences are contained between the detection sequences, between the detection sequence and the sequence complementary to the detection sequence and between the sequences complementary to the detection sequences, respectively.

The term "capable of hybridizing" or "hybridization" as used herein refers to a fact that bases form base pairs through a hydrogen bond to form a double-stranded nucleic acid molecule. The hybridization between the detection probe and an amplification product of the target nucleic acid is carried out under conditions that are stringent to such an extent that, when there is a mismatch due to which no base pair is formed between a sequence and a sequence complementary to the sequence, the formation of a double strand between the detection probe and a nucleic acid including a sequence having the mismatch can be suppressed or inhibited. The term "stringent conditions" as used herein refers to conditions which are generally employed by persons skilled in the art in the hybridization between polynucleotides. Stringent conditions are such conditions that a given single-stranded polynucleotide can hybridize with another single-stranded polynucleotide that has a certain degree of complementarity thereto and cannot substantially hybridize with a single-stranded polynucleotide that does not have complementarity thereto. It is known that temperatures, salt concentrations, chain lengths of polynucleotides to be hybridized, the GC contents in the polynucleotides, the concentration of a chaotropic agent in a hybridization buffer solution to be used and the like are involved in the degree of stringency in hybridization. The stringent conditions can be set appropriately by a person skilled in the art by reference to, for example, the conditions mentioned in Sambrook, J. et al. (1998) Molecular Cloning: A Laboratory Manual (2nd ed.), Cold Spring Harbor Laboratory Press, New York.

In the nucleic acid detection step, the amplification of a nucleic acid in a sample may be carried out prior to the below-mentioned compartment preparation step (wherein the amplification step is also referred to as "a pre-amplification step", hereinafter). For example, in the case where the concentration of the target nucleic acid in the sample is low, the detection of the target nucleic acid can become easy by amplifying the target nucleic acid prior to the compartment preparation step. The method for the nucleic acid amplification in the pre-amplification step is not particularly limited. For example, a polymerase chain reaction (PCR) method, a RT-PCR method, a nucleic acid sequence based amplification (NASBA) method and a transcription-mediated amplification (TMA) method are exemplified. The pre-amplification step can be carried out before and/or after the sample preparation step. In the case where the pre-amplification step is carried out after the sample preparation step, the quality control polynucleotide is also amplified by the pre-amplification.

In the nucleic acid detection step in the first aspect, the compartment preparation step is carried out. Examples of the "compartment" include a microwell on a substrate and an aqueous droplet in an oily phase. More specifically, compartments prepared by employing the methods described in the specifications of U.S. Pat. Nos. 7,842,457 and 8,048,627 are exemplified. The compartments may be those which are prepared using a commercially available digital PCR system such as QuantStudio (trade name) 3D digital PCR system (Thermo Fisher Scientific Inc.), QX200 (trade name) Droplet Digital (trade name) PCR analysis system (Bio-Rad Laboratories, Inc.), Biomark (trade name) HD MX/HX system (Fluidigm Corporation), and Rain Drop system (RainDance Technologies, Inc.).

In general, a larger number of compartments than the number of molecules of the target nucleic acid or the quality control polynucleotide are used. Therefore, multiple compartments in each of which only one molecule of the target nucleic acid or the quality control polynucleotide is contained theoretically are prepared. A large number of compartments in each of which no target nucleic acid or quality control polynucleotide is contained are also prepared.

Each compartment contains the below-mentioned reagent that is needed for the nucleic acid amplification. The reagent can be selected appropriately by a person skilled in the art, and generally includes a nucleic acid amplification primer, dNTPs (dATP, dCTP, dGTP, and dTTP or dUTP), a polymerase, a buffering agent and the like. The primer may be immobilized onto a solid support such as a substrate and a bead.

In the nucleic acid detection step in the first aspect, the nucleic acid amplification of a nucleic acid contained in a nucleic acid sample is carried out in each compartment. In the case where a target nucleic acid is present in the compartment, an amplification product of the target nucleic acid is produced. In the case where a quality control polynucleotide is present in the compartment, an amplification product of the quality control polynucleotide is produced. The amplification product is produced in the compartment (this amplification is also referred to as "digital nucleic acid amplification" in the specification).

Examples of the method for the nucleic acid amplification include, but are not limited to, a PCR method, an RT-PCR method, an NASBA method and a TMA method. In one embodiment, the method for the nucleic acid amplification is a PCR. A PCR at a level of one molecule of a nucleic acid is also called a "digital PCR". The digital PCR may be, for example, an emulsion PCR in which droplets are used as the compartments (which is also referred to as "droplet-type digital PCR", hereinafter) or digital PCR in which reaction wells are used as the compartments (wherein this type of digital PCR is also referred to as a "well-type digital PCR", hereinafter). The PCR may be carried out, for example, in three steps of (1) thermal denaturation, (2) annealing and (3) extension, or in two steps of (1) thermal denaturation and (2') annealing and extension wherein (2) annealing or hybridization and (3) extension are carried out under the same temperature conditions as each other. The conditions for each step can be set appropriately. The change in temperature in each step can be controlled automatically using a thermal cycler such as Veriti thermal cycler (Applied Biosystems).

In the nucleic acid detection step in the first aspect, a signal detection step using a detection probe is carried out. In the signal detection step in one embodiment, the detection probe is first hybridized with the amplification products under stringent conditions. When a signal that indicates the presence of the detection sequence is detected, it is determined that an amplification product containing the detection sequence is present. When a signal that indicates the presence of the detection sequence is not detected, it is determined that an amplification product containing the detection sequence is absent.

The "detection probe" contains an oligonucleotide containing a sequence complementary to the detection sequence. Multiple types of detection probes may be used. For example, in the case where the presence or absence of a nucleotide mutation in the target sequence is to be analyzed, both a detection probe capable of hybridizing with a mutant sequence of the target sequence (wherein the detection probe is also referred to as a "mutant detection probe", hereinafter) and a detection probe capable of hybridizing with the wild-type sequence of the target sequence (wherein the detection probe is also referred to as a "wild-type detection probe", hereinafter) can be used. These detection probes generate different types of signals from each other. In one example, the wavelength of fluorescence originated from the mutant detection probe and the wavelength of fluorescence originated from the wild-type detection probe are different from each other. The presence or absence of a mutation in the target sequence can be analyzed depending on what wavelength is detected at what level.

The detection probe to be used in the present disclosure may be an oligonucleotide that is labeled with a labeling substance previously or an unlabeled oligonucleotide. From the viewpoint of detection sensitivity, it is preferred to use a labeled oligonucleotide.

Examples of the labeling substance include a fluorescent substance, an enzyme and a hapten. In the specification, the previously labeled detection probe is also referred to as a "labeled detection probe". In the case where a fluorescent substance is used as the labeling substance, fluorescence is detected in the form of a signal. Examples of the fluorescent substance include fluorescein, rhodamine, Texas red, tetramethyl rhodamine, carboxy rhodamine, phycoerythrin, 6-FAM (trade name), Cy (registered trade name) 3, Cy (registered trade name) 5, and products of Alexa Fluor (registered trade name) series. In the case where an enzyme is used as the labeling substance, a signal (e.g., luminescence) can be detected by reacting a substrate for the enzyme with the enzyme to produce a reaction product that emits the signal. In the case where a hapten is used as the labeling substance, an enzyme or a fluorescent substance is bound to the detection probe through a substance capable of binding specifically to the hapten. In this manner, a signal such as fluorescence or luminescence can be detected. An example of the substance capable of binding specifically to a hapten is an anti-hapten antibody. In the case where biotin is used as the hapten, an avidin compound (e.g., avidin, streptavidin) can also be used.

It is considered that the influence (e.g., steric hindrance) of the labeling substance on the hybridization between the labeled detection probe and a nucleic acid containing the detection sequence is small. Therefore, it is preferred that the labeling substance in the labeled detection probe labels (modifies) the detection probe at the 5'- and/or 3'-terminal thereof. The detection probe may contain a supplementary sequence at the 5'- and/or 3'-terminal of a sequence complementary to the detection sequence. The labeled detection probe may contain a supplementary sequence at the 5'- and/or 3'-terminal of a sequence complementary to the detection sequence, wherein the 5'- and/or 3'-terminal may be labeled with the labeling substance. It is considered that, in such a labeled detection probe, the influence of the labeling substance on the hybridization between the labeled detection probe and a nucleic acid containing the detection sequence is reduced compared with a labeled detection probe which contains no supplementary sequence and is labeled with a labeling substance at the 5'- and/or 3'-terminal thereof. The supplementary sequence may be a non-complementary sequence in which base pairs are not formed in a part or the whole area thereof with an opposed sequence upon the hybridization of the labeled detection probe with a nucleic acid containing the detection sequence, or may be a complementary sequence in which base pairs are formed in the whole area thereof with the opposed sequence.

In one embodiment, the labeled detection probe is labeled with the labeling substance at the 5'-terminal thereof.

In another embodiment, the detection probe is a non-labeled oligonucleotide. In the case where a non-labeled oligonucleotide is used, the detection of a signal can be achieved using a fluorescent substance such as an intercalator.

In another embodiment, a combination of a fluorescent substance and a quencher substance may be used as the labeling substance. In the case where two types of labeling substances are used as mentioned above, it is possible, for example, to label the 5'-terminal of the detection probe with one of the fluorescent substance and the quencher substance and to label the 3'-terminal of the detection probe with the other labeling substance. Specific examples of the detection probe labeled with two types of labeling substances include TaqMan (trade name) probe and Molecular Beacon. These probes are known and are mentioned in many published materials, patent documents and other documents. For example, as for TaqMan (trade name) probe, see U.S. Pat. No. 5,538,848 or the like; and as for Molecular Beacon, see U.S. Pat. No. 5,925,517 or the like. The entire contents disclosed in these documents are incorporated herein by reference. The term "quencher substance" as used herein refers to a substance having an activity of reducing or quenching fluorescence.

The detection of a signal originated from the detection probe can be carried out, but not limited to, using a detector that is suitable for the detection of signals originated from compartments or beads (see Embodiment 1 mentioned below) which can be present in a large number (e.g., tens of millions). Examples of the detector to be used include, but are not limited to, a microscope, a flow cytometer and an image sensor.

A "flow cytometer" is a device which can count the number of particles (e.g., beads) or compartments (e.g., droplets) by irradiating the particles or compartments with excitation light in a flow cell and obtaining optical information (e.g., fluorescence) emitted from the individual particles or compartments. A flow cytometer is preferred, because many particles or compartments can be measured within a short time.

In the case where a microscope or an image sensor is used, the individual beads or compartments can be detected by imaging a field of view and detecting the beads or compartments by using the imaged data. In the case where beads are used, the beads may remain at rest or may be flowing. A fluorescence microscope or the like can be used depending on the types of the signal.

In the case where the detection of a signal is carried out while retaining the compartments prepared in the compartment preparation step, the detection probe is added to the reaction system in the compartment preparation step or any step proceeding to the compartment preparation step.

In the case where the amplification product is immobilized onto beads or the like, the detection of a signal may be carried out while retaining the compartments, or the beads may be removed from the compartments and dispersed in an aqueous solvent prior to the detection of the signal. The method for removing the beads from the compartments prior to the detection of a signal is not limited particularly. For example, in the case where aqueous droplets in an oily phase are used as the compartments, it is possible to remove the oily phase and disperse the liquid phase in an aqueous solvent. In the case where wells each containing beads are used as the compartments, it is possible to wash each of the wells to remove the beads from the wells and then disperse the beads in an aqueous solvent. When the beads are removed from the compartments, the detection probe may be added to the reaction system in the compartment preparation step, or the detection probe may be hybridized with the amplification product after the removal of the beads.

In the determination step in the first aspect, it is determined as to whether or not the nucleic acid detection step is proper on the basis of the result of the signal detection step. Hereinbelow, an example in which a signal comes from a compartment will be described.

In the determination step, first it is determined as to whether or not each of the compartments is a compartment in which an amplification product of a nucleic acid is produced. A compartment in which a signal is detected (i.e., a positive compartment) is determined as a compartment in which an amplification product of the nucleic acid is produced, and a compartment in which no signal is detected (i.e., a negative compartment) is determined as a compartment in which no amplification product of the nucleic acid is produced.

In the determination on positiveness, it is preferred to compare a predetermined threshold value with the intensity of a signal detected in a compartment (wherein a threshold value used in the determination on positiveness is also referred to as a "first threshold value"). It is often the case that a solid support, such as a well, has a signal (e.g., autofluorescence) by its nature. For example, in the case where a well contains a bead and the bead has autofluorescence by its nature, weak fluorescence may be detected as a signal from the well. In order to determine the compartment as a negative compartment, the above-mentioned first threshold value is used.

The intensity of fluorescence originated from an amplification product of the target nucleic acid is different from the intensity of fluorescence originated from an amplification product of the quality control polynucleotide. In order to distinguish these intensities from each other, a second threshold value may be used. The second threshold value is larger than the first threshold value. In the case where the intensity of fluorescence originated from an amplification product of the quality control polynucleotide is larger than the intensity of fluorescence originated from an amplification product of the target nucleic acid, it can be determined that a positive compartment having a fluorescence intensity that is equal to or larger than the first threshold value and is smaller than the second threshold value (which is also referred to as a "first positive compartment", hereinafter) is a compartment in which an amplification product of the target nucleic acid is produced. It can be determined that a positive compartment having a fluorescence intensity that is equal to or larger than the second threshold value (which is also referred to as a "second positive compartment", hereinafter) is a compartment in which an amplification product of the quality control polynucleotide is produced.

Alternatively, it also be possible to determine a compartment in which no signal is detected (i.e., a negative compartment) as a compartment in which no amplification product of the nucleic acid is produced. When the signal coming from a compartment is smaller than the first threshold value, it can be determined that the compartment is a negative compartment.

In the case where a bead onto which a primer is immobilized is used and a signal coming from the bead is detected, it is possible to remove the bead from each of the compartments and the determination on positiveness/negativeness may be carried out with respect to each bead rather than each compartment. In this case, the determination on positiveness/negativeness of a bead can be carried out in the same manner as for the determination on positiveness/negativeness of a compartment. That is, it is possible to determine a bead in which the signal intensity is equal to or larger than the first threshold value and is smaller than the second threshold value as a first positive bead, and determine a bead in which the signal intensity is equal to or larger than the second threshold value as a second positive bead. It is also possible to determine a bead which generates a signal having an intensity smaller than the first threshold value as a negative bead.

In the case where signals coming from beads are to be detected with a flow cytometer, beads removed from each of compartments are allowed to flow in a flow cell and a signal coming from the individual bead is detected. In this case, it is possible that a two-dimensional scattergram (also referred to as a "2D scattergram", hereinafter) on which signal intensities of beads are plotted is produced and a cluster of first positive beads and a cluster of second positive beads are distinguished from each other on the scattergram to evaluate the first positive beads and the second positive beads. The same procedure can be carried out in the case where the detection of signals is carried out by allowing compartments themselves to flow in a flow cell regardless of the presence or absence of beads in the compartments.

Subsequently, it is determined as to whether or not the nucleic acid detection step is proper on the basis of the result of the determination of the positive compartments or the positive beads which is obtained in the determination step.

For example, the number of the second positive compartments is counted and it can be determined that the nucleic acid detection step is proper when the count result is equal to or larger than a third threshold value. When the count result is smaller than the third threshold value, it is considered that the quality control polynucleotide is not amplified normally. In this case, it can be determined that the nucleic acid detection step is improper. In this example, the comparison between the count result for the second positive compartments and the threshold value is carried out. However, the same determination can also be made by employing the sum total of fluorescence intensities coming from the second positive compartments or the sum total of areas in each of which fluorescence is generated. The same determination can also be made in the case where beads are used.

The first threshold value and the second threshold value can be set appropriately depending on the types of the labeling substances, the intensities of signals and the like. It is possible to detect the level of the signal intensity of a positive compartment or a positive bead in advance using multiple nucleic acid samples and set a threshold value to such a value at which negativeness, first positiveness and second positiveness can be distinguished from one another with highest accuracy.

The third threshold value can be set appropriately on the basis of the concentration (the number of copies) of the quality control polynucleotide in a nucleic acid sample, or the like.

[Quality Control in Detection of Mutation]

The method for controlling quality of nucleic acid amplification (also referred to as "nucleic acid amplification quality control method", hereinafter) according to the first aspect can apply to a method for controlling quality in the detection of a mutation in a target nucleic acid. Therefore, one embodiment of the first aspect is a method for controlling quality in the detection of a mutation in a target nucleic acid.

The term "mutation" as used herein refers to a fact that a nucleotide sequence of a nucleic acid of interest is different from a sequence that is recognized as a wild-type sequence for the nucleic acid of interest. For example, the type of the mutation includes substitution, deletion, addition, chromosomal translocation and the like of a nucleotide in a nucleic acid. Specific examples of the mutation include a point mutation and a single nucleotide polymorphism (SNP). The mutation may be a substitution, deletion or insertion.

In the detection of a mutation, it is detected as to whether or not the target nucleic acid is of a mutant form or a wild-type. In the detection of a mutation in a target nucleic acid, a detection probe capable of hybridizing with a mutant form of the target nucleic acid and a detection probe capable of hybridizing with a wild-type of the target nucleic acid are used for an amplification product of the target nucleic acid to determine as to which detection probe hybridizes with the amplification product, thereby determining as to whether or not the target nucleic acid is of a mutant form or a wild-type. In a mutant form of the target nucleic acid, a mutant form of the detection sequence (wherein the mutant form is also referred to as a "Mut detection sequence", hereinafter) is contained. In the wild-type of the target nucleic acid, the wild-type of the detection sequence (wherein the wild-type is also referred to as a "Wt detection sequence", hereinafter) is contained. Hereinbelow, the method for controlling quality in the detection of a mutation in the target nucleic acid will be described as one embodiment.

The method according to this embodiment includes a nucleic acid detection step and a determination step. The nucleic acid detection step includes a nucleic acid sample preparation step, a compartment preparation step, a nucleic acid amplification step and a signal detection step, like the above-mentioned method.

In the nucleic acid sample preparation step in this embodiment, a sample containing a target nucleic acid is mixed with a sample containing a quality control polynucleotide to prepare a nucleic acid sample, for example.

As the quality control polynucleotide, one or both of a quality control polynucleotide for use in the detection of a Mut detection sequence (wherein the quality control polynucleotide is also referred to as a "Mut quality control polynucleotide", hereinafter) and a quality control polynucleotide for use in the detection of a Wt detection sequence (wherein the quality control polynucleotide is also referred to as a "Wt quality control polynucleotide", hereinafter) are used. The Mut quality control polynucleotide contains one or both of a Mut detection sequence to which the below-mentioned mutant detection probe can bind and a sequence complementary to the Mut detection sequence. Therefore, an amplification product of the Mut quality control polynucleotide can bind to the mutant detection probe to generate a signal originated from the mutant detection probe. The Wt quality control polynucleotide contains one or both of a Wt detection sequence to which the below-mentioned wild-type detection probe can bind and a sequence complementary to the Wt detection sequence. Therefore, an amplification product of the Wt quality control polynucleotide can bind to the wild-type detection probe to generate a signal originated from the wild-type detection probe.

In the case where only the below-mentioned mutant detection probe is used as the detection probe, it is preferred to use at least the Mut quality control polynucleotide. In the case where both of the mutant detection probe and the wild-type detection probe are used as the detection probes, it is preferred to use one or both of the Mut quality control polynucleotide and the Wt quality control polynucleotide.

With respect to other characteristic properties of the above-mentioned quality control polynucleotide, the same can apply to the Mut quality control polynucleotide and the Wt quality control polynucleotide.

The compartment preparation step in this embodiment, nucleic acid amplification step and signal detection step can be carried out in the same manner as mentioned above with regard to the first aspect.

As the detection probe, a mutant detection probe containing a sequence complementary to the Mut detection sequence can be used. In the case where a mutation is contained in the target nucleic acid, the mutant detection probe can bind to an amplification product of the target nucleic acid, and therefore a signal originated from the mutant detection probe can be detected. It is preferred to additionally use a wild-type detection probe containing a sequence complementary to the Wt detection sequence as the detection probe. The signal originated from the mutant detection probe and the signal originated from the wild-type detection probe are different from each other. For example, it is possible to use an FAM-labeled oligonucleotide as the wild-type detection probe and use a Cy5-labeled oligonucleotide as the mutant detection probe. With respect to the characteristic properties of the wild-type detection probe and the mutant detection probe mentioned above, the same can apply to this mutant detection probe and this wild-type detection probe.

In the signal detection step in this embodiment, the detection of a signal originated from the detection probe is carried out. In the case where both the mutant detection probe and the wild-type detection probe are used, both a signal originated from the mutant detection probe and a signal originated from the wild-type detection probe are detected.

In the determination step in this embodiment, it is determined as to whether or not a mutation is present and whether or not the nucleic acid detection step is proper on the basis of the result obtained in the signal detection step.

In this regard, first an example in which only a mutant detection probe is used as the detection probe is described. In this example, a nucleic acid sample prepared in the nucleic acid sample preparation step contains a target nucleic acid, a Mut quality control polynucleotide and beads. In the nucleic acid amplification step, beads to each of which an amplification product of the target nucleic acid is bound and beads to each of which an amplification product of the Mut quality control polynucleotide is bound can be produced. The beads are removed from the compartments prior to the signal detection step. The beads removed from the compartments are dispersed in an aqueous medium, and then a mutant detection probe is added thereto.

In the determination step, as mentioned above, it is determined as to whether or not each of the beads is a bead to which an amplification product of the nucleic acid is bound. The hybridization between an amplification product of the target nucleic acid and an amplification product of the quality control polynucleotide with the detection probe is carried out under stringent conditions. A signal originated from the mutant detection probe is detected in the beads to each of which an amplification product of the target nucleic acid containing the Mut detection sequence is bound and the beads to each of which an amplification product of the Mut quality control polynucleotide is bound. On the other hand, a signal originated from the mutant detection probe is not detected in the beads to each of which an amplification product of the target nucleic acid containing the Wt detection sequence is bound.

The beads in each of which a signal originated from the mutant detection probe is not detected (i.e., negative beads) are determined as beads to each of which an amplification product of the nucleic acid is not bound or beads to each of which an amplification product of the target nucleic acid containing the Wt detection sequence is bound. The beads in each of which a signal originated from the mutant detection probe is detected (i.e., positive beads) are determined as beads to each of which an amplification product of a nucleic acid which contains the Mut detection sequence is bound. In this determination on positiveness, a threshold value associated with the intensity of a signal (i.e., a first threshold value) may be used, as mentioned above.

As mentioned above, the intensity of a signal originated from an amplification product of the target nucleic acid is different from the intensity of a signal originated from an amplification product of the quality control polynucleotide. In order to distinguish these signal intensities, a second threshold value may be used.

When the intensity of a signal originated from an amplification product of the Mut quality control polynucleotide is larger than the intensity of a signal originated from an amplification product of the target nucleic acid containing the Mut detection sequence, positive beads, i.e., beads in each of which the signal intensity is equal to or larger than the first threshold value and smaller than the second threshold value, (wherein the positive beads are also referred to as "first positive beads", hereinafter), can be determined as beads to each of which an amplification product of the target nucleic acid containing the Mut detection sequence is bound. Positive beads, i.e., beads in each of which the signal intensity is equal to or larger than the second threshold value (wherein the beads are also referred to as "second positive beads", hereinafter), can be determined as beads to each of which an amplification product of the Mut quality control polynucleotide is bound.

In the determination step, the determination on the presence or absence of a mutation in the target nucleic acid is carried out. For example, in the determination on the presence or absence of a mutation, the number of the first positive beads is counted and it can be determined that a mutation occurs (i.e., positive) when the count result is equal to or larger than the third threshold value. The number of the first positive beads is counted, and it can be determined that no mutation occurs (i.e., negative) when the count result is smaller than the third threshold value.

In this example, the count result for the first positive beads is compared with a threshold value. However, the same determination can also be made using the sum total of the fluorescence intensities from the first positive beads.

In this example, the beads are removed from the compartments. However, the same determination can also be made on the basis of the result of the detection of signals originated from the compartments while retaining the beads in the compartments. The same determination can also be made by carrying out the nucleic acid sample preparation step, the compartment preparation step and the nucleic acid amplification step without using beads, then carrying out the signal detection step while retaining the compartments, and then carrying out the determination step on the basis of the result of the detection of signals coming from the compartments.

Subsequently, it is determined as to whether or not the nucleic acid detection step is proper in the determination step.

For example, the number of the second positive beads is counted. When the count result is equal to or larger than the third threshold value, it can be determined that the nucleic acid detection step is proper. When the count result for the second positive beads is smaller than the third threshold value, it can be determined that the nucleic acid detection step is improper. The third threshold value for the number of beads can be set appropriately depending on the concentration (number of copies) of the quality control polynucleotide in a nucleic acid sample and the like.

When it is determined that the nucleic acid detection step is proper, it can be determined that the result of the determination on the presence or absence of a mutation in the target nucleic acid is reliable. When it is determined that the nucleic acid detection step is improper, the result of the determination on the presence or absence of a mutation in the target nucleic acid is not reliable. In this case, it can be determined that there is a possibility that the result of the determination on the detection of a mutation in the target nucleic acid, i.e., positive or negative, is false-positive or false-negative, respectively. Thus, according to one embodiment of the first aspect, a result that it is doubtful about whether the result of the determination on the detection of a mutation in the target nucleic acid is false-positive or false-negative can be provided. In this manner, the quality in the detection of a mutation in the target nucleic acid can be improved.

When it is determined that the nucleic acid detection step is improper, it is predicted that either one of the steps in the nucleic acid detection step is improper. Thus, according to this embodiment, it becomes possible to appropriately identify an improper step in the detection of a mutation in the target nucleic acid by providing a determination result that the nucleic acid detection step is improper.

Next, an example in which both the mutant detection probe and the wild-type detection probe are used in the determination step will be described. In this example, a nucleic acid sample prepared in the nucleic acid sample preparation step contains the target nucleic acid, the Mut quality control polynucleotide, the Wt quality control polynucleotide and beads. In the nucleic acid amplification step, beads to each of which an amplification product of the target nucleic acid is bound, beads to each of which an amplification product of the Mut quality control polynucleotide is bound and beads to each of which an amplification product of the Wt quality control polynucleotide is bound are produced. The beads are removed from the compartments prior to the signal detection step. The beads removed from the compartments are dispersed in an aqueous medium, and then the mutant detection probe and the wild-type detection probe are added to the dispersion.

A signal originated from the mutant detection probe is detected but a signal originated from a wild-type detection probe is not detected in the beads to each of which an amplification product of the target nucleic acid containing the Mut detection sequence is bound and the beads to each of which an amplification product of the Mut quality control polynucleotide is bound. Similarly, a signal originated from the wild-type detection probe is detected but a signal originated from the mutant detection probe is not detected in the beads to each of which an amplification product of the target nucleic acid containing the Wt detection sequence is bound and an amplification product of the Wt quality control polynucleotide is bound.

Beads in each of which neither a signal originated from the mutant detection probe nor a signal originated from the wild-type detection probe is detected (i.e., negative beads) can be determined as beads to each of which an amplification product of the nucleic acid is not bound. Beads in each of which a signal originated from one of the mutant detection probe and the wild-type detection probe is detected and a signal originated from the other is not detected (i.e., positive beads) can be determined as beads to each of which an amplification product of the nucleic acid is bound. As mentioned above, in this determination on positiveness, a threshold value for the intensity of a signal (i.e., the first threshold value) may be used. That is, a "first threshold value (Wt)" may be used as the first threshold value to be compared with the intensity of a signal originated from the wild-type detection probe, and a "first threshold value (Mut)" may be used as the first threshold value to be compared with the intensity of a signal originated from the mutant detection probe.

As mentioned above, the intensity of a signal originated from an amplification product of the target nucleic acid and the intensity of a signal originated from an amplification product of the quality control polynucleotide are different from each other. In order to distinguish these signal intensities from each other, second threshold values can be used respectively for the signals originated from the detection probes. That is, a "second threshold value (Wt)" may be used as the second threshold value for the intensity of a signal originated from the wild-type detection probe, and a "second threshold value (Mut)" may be used as the second threshold value for the intensity of a signal originated from the mutant detection probe. A second threshold value for each signal is higher than a first threshold value for the signal.

Hereinbelow, a case where the intensity of a signal originated from an amplification product of the Mut quality control polynucleotide is larger than the intensity of a signal originated from an amplification product of the target nucleic acid containing the Mut detection sequence and the intensity of a signal originated from an amplification product of the Wt quality control polynucleotide is larger than the intensity of a signal originated from an amplification product of the target nucleic acid containing the Wt detection sequence in this example will be described.

Positive beads in each of which the signal intensity is equal to or larger than the first threshold value (Mut) and smaller than the second threshold value (Mut) and smaller than the first threshold value (Wt) (wherein the beads are also referred to as "first positive beads (Mut)", hereinafter) can be determined as beads to each of which an amplification product of the target nucleic acid containing the Mut detection sequence is bound. Positive beads in each of which the signal intensity is equal to or larger than the second threshold value (Mut) and smaller than the first threshold value (Wt) (wherein the beads are also referred to as "second positive beads (Mut)", hereinafter) can be determined as beads to each of which an amplification product of the Mut quality control polynucleotide is bound. Positive beads in each of which the signal intensity is equal to or larger than the first threshold value (Wt) and smaller than the second threshold value (Wt) and smaller than the first threshold value (Mut) (wherein the beads are also referred to as "first positive beads (Wt)", hereinafter) can be determined as beads to each of which an amplification product of the target nucleic acid containing the Wt detection sequence is bound. Positive beads in each of which the signal intensity is equal to or larger than the second threshold value (Wt) and smaller than the first threshold value (Mut) (wherein the beads are also referred to as "second positive beads (Wt)", hereinafter) can be determined as beads to each of which an amplification product of the Wt quality control polynucleotide is bound.

In the determination step, as mentioned above, the determination on the presence or absence of a mutation is carried out. For example, the determination on the presence or absence of a mutation can be made by employing, as a measure, a matter that how much concentration (how many number of copies) of the target nucleic acid, among the total concentration (total number of copies) of the target nucleic acid, contains the Mut detection sequence (i.e., the ratio of the number of copies of the target nucleic acid containing the Mut detection sequence to the total number of copies of the target nucleic acid: (the number of copies of the target nucleic acid containing the Mut detection sequence)/(the total number of copies of the target nucleic acid)). This ratio can be calculated by dividing the number of the first positive beads (Mut) by the total number of the first positive beads (Mut) and the first positive beads (Wt) (=(the number of the first positive beads (Mut))/[(the number of the first positive beads (Mut))+(the number of the first positive beads (Wt))]). When the calculated ratio is equal to or larger than a third threshold value for this ratio, it can be determined that a mutation occurs (i.e., positive). When the ratio is smaller than the predetermined threshold value, it can be determined that no mutation occurs (i.e., negative). The measure to be employed for the determination is not limited to this ratio. As mentioned above, it is also possible to determine that a mutation occurs (i.e., positive) when the number of the first positive beads (Mut) is equal to or larger than a third threshold value for the number of beads, and determine that no mutation occurs (i.e., negative) when the number of the first positive beads (Mut) is smaller than the third threshold value.

In the determination step, the determination as to whether or not the nucleic acid detection step is proper is made.

For example, the number of the second positive beads (Mut) and the number of the second positive beads (Wt) are counted separately.

When the count result for the second positive beads (Mut) is smaller than the third threshold value (Mut) or the count result for the second positive beads (Wt) is smaller than the third threshold value (Wt), it can be determined that the nucleic acid detection step is improper and the result of the detection on the presence or absence of a mutation is less reliable. In this case, the result of the detection on the presence or absence of a mutation may be output with a note "less reliable" or may not be output.

When the count result for the second positive beads (Mut) is equal to or larger than the third threshold value (Mut) and the count result for the second positive beads (Wt) is equal to or larger than the third threshold value (Wt), it can be determined that the nucleic acid detection step is proper. In this case, a note "reliable" can be added to the result of the detection on the presence or absence of a mutation.

When the count result for the second positive beads (Mut) is smaller than a third threshold value for the second positive beads (Mut), it can be determined that the nucleic acid detection step for the target nucleic acid containing the Mut detection sequence is improper. Thus, it can be determined that the result of the determination on the presence or absence of a mutation in the target nucleic acid is not reliable. In this case, there is a possibility that it is determined that the result of the determination on the detection of a mutation in the target nucleic acid, i.e., positive or negative, may be false-positive or false-negative, respectively. As mentioned above, a supplementary test for verifying as to which step in the nucleic acid detection step is improper may be carried out, if necessary.

In the above-mentioned example, the beads are removed from the compartments. However, the same determination can also be made on the basis of the result of the detection of a signal originated from each of the compartments while retaining the beads in the compartments. It is also possible to carry out the nucleic acid sample preparation step, the compartment preparation step and the nucleic acid amplification step without using beads, subsequently carry out the signal detection step while retaining the compartments, and subsequently carry out the determination step in the same manner as mentioned above on the basis of the result of the detection of a signal originated from each of the compartments.

In the above-mentioned method for controlling quality in the detection of a mutation, two types of quality control polynucleotides are used. Hereinbelow, an example in which the method for controlling quality in the detection of a mutation can be carried out using one type of quality control polynucleotide will be described. The quality control polynucleotide to be used in this example contains one or both of the Wt detection sequence and a sequence complementary to the detection sequence and one or both of the Mut detection sequence and a sequence complementary to the detection sequence in the third region thereof (wherein the quality control polynucleotide is also referred to as a "Wt & Mut quality control polynucleotide", hereinafter).

In this example, the nucleic acid sample prepared in the nucleic acid sample preparation step contains the target nucleic acid, the Wt & Mut quality control polynucleotide and beads. In the nucleic acid amplification step, beads to each of which an amplification product of the target nucleic acid is bound and beads to each of which an amplification product of the Wt & Mut quality control polynucleotide is bound can be produced. The beads can be removed from the compartments prior to the signal detection step. The beads removed from the compartments are dispersed in an aqueous medium, and then the mutant detection probe and the wild-type detection probe are added to the dispersion.

In the detection step in this embodiment, the same signal as mentioned above can be obtained from each of the beads to each of which an amplification product of the target nucleic acid is bound.

The Wt & Mut quality control polynucleotide contains both the Wt detection sequence and the Mut detection sequence. Therefore, when an amplification product of the Wt & Mut quality control polynucleotide and the detection probe are hybridized with each other under stringent conditions, a signal originated from the mutant detection probe and a signal originated from the wild-type detection probe can be produced.

Beads in each of which a signal originated from the mutant detection probe is not detected and a signal originated from the wild-type detection probe is not detected (i.e., negative beads) are determined as beads to each of which an amplification product of the nucleic acid is not bound. Beads in each of which both a signal originated from the mutant detection probe and a signal originated from the wild-type detection probe are detected are determined as beads to each of which an amplification product of the Wt & Mut quality control polynucleotide is bound (wherein the beads are also referred to as "Wt & Mut positive beads", hereinafter).

In this determination on positiveness, as mentioned above, a threshold value for the intensity of a signal (i.e., a first threshold value) may be used. That is, a "first threshold value (Wt)" may be used as the first threshold value which is to be compared with the intensity of a signal originated from the wild-type detection probe, and a "first threshold value (Mut)" may be used as the first threshold value which is to be compared with the intensity of a signal originated from the mutant detection probe.

The total number of Wt detection sequences and sequences complementary to the detection sequences in an amplification product of the Wt & Mut quality control polynucleotide is different from the total number of Wt detection sequences and sequences complementary to the detection sequences in an amplification product of the target nucleic acid containing the Wt detection sequence. Similarly, the total number of Mut detection sequences and sequences complementary to the detection sequences in an amplification product of the Wt & Mut quality control polynucleotide is different from the total number of Mut detection sequences and sequences complementary to the detection sequences in an amplification product of the target nucleic acid containing the Mut detection sequence. Therefore, the intensity of a signal originated from each of the detection probes in an amplification product of the target nucleic acid is different from the intensity of a signal originated from the each of the detection probes in an amplification product of the Wt & Mut quality control polynucleotide. In order to distinguish between these signal intensities, a second threshold value can be used for a signal originated from each of the detection probes. That is, a "second threshold value (Wt)" can be used as the second threshold value for the intensity of a signal originated from the wild-type detection probe, and a "second threshold value (Mut)" can be used as the second threshold value for the intensity of a signal originated from the mutant detection probe. The second threshold value for a signal is higher than the first threshold value for the signal.

Hereinbelow, a case where the intensity of a signal originated from an amplification product of the Wt & Mut quality control polynucleotide is larger than the intensity of a signal originated from an amplification product of the target nucleic acid containing the Wt detection sequence and the intensity of a signal originated from an amplification product of the Wt & Mut quality control polynucleotide is larger than the intensity of a signal originated from an amplification product of the target nucleic acid containing the Mut detection sequence in this example will be described. Positive beads in each of which the signal intensity is equal to or larger than the first threshold value (Mut) and smaller than the second threshold value (Mut) and smaller than the first threshold value (Wt) (i.e., first positive beads (Mut)) can be determined as beads to each of which an amplification product of the target nucleic acid containing the Mut detection sequence is bound. Positive beads in each of which the signal intensity is equal to or larger than the first threshold value (Wt) and smaller than the second threshold value (Wt) and smaller than the first threshold value (Mut) (i.e., first positive beads (Wt)) can be determined as beads to each of which an amplification product of the target nucleic acid containing the Wt detection sequence is bound. Positive beads in each of which the signal intensity is equal to or larger than the second threshold value (Wt) and equal to or larger than the second threshold value (Mut) (wherein the beads are also referred to as "second positive beads (Wt & Mut)", hereinafter) can be determined as beads to which an amplification product of the Wt & Mut quality control polynucleotide is bound (i.e., Wt & Mut positive beads).

In the determination step, the presence or absence of a mutation is determined in the same manner as in the above-mentioned embodiment. For example, it can be determined that a mutation occurs (i.e., positive) when the number of the first positive beads (Mut) is equal to or larger than a third threshold value for the number of the first positive beads (Mut), and it can be determined that no mutation occurs (i.e., negative) when the number of the first positive beads (Mut) is smaller than the third threshold value. As mentioned above, the determination on the presence or absence of a mutation can be made by employing, as a measure, a matter that how much concentration (how many number of copies) of the target nucleic acid, among the total concentration (total number of copies) of the target nucleic acid, contains the Mut detection sequence. This method is just illustrative, and the method for determining the presence or absence of a mutation is not limited thereto.

In the determination step, the determination as to whether or not the nucleic acid detection step is proper is made.

The determination step in a quality control method in which one type of a Wt & Mut quality control polynucleotide is used is carried out in the same manner as the determination step in the above-mentioned quality control method in which two types of quality control polynucleotides, i.e., a Wt quality control polynucleotide and a Mut quality control polynucleotide, are used, except for the below-mentioned matters.

In the above-mentioned quality control method in which two types of quality control polynucleotides, i.e., a Wt quality control polynucleotide and a Mut quality control polynucleotide, are used, the determination as to whether or not the nucleic acid detection step for the target nucleic acid containing the Wt detection sequence is proper is made from the second positive beads (Wt). The determination as to whether or not the nucleic acid detection step for the target nucleic acid containing the Mut detection sequence is proper is made from the second positive beads (Mut). That is, in the case where two types of quality control polynucleotides are used, the determination as to whether or not the nucleic acid detection step for the target nucleic acid containing the Wt detection sequence and the nucleic acid detection step for the target nucleic acid containing the Mut detection sequence are proper is made from two types of positive beads.

In the quality control method in which only one type of Wt & Mut quality control polynucleotide is used as the quality control polynucleotide, in contrast, the determination as to whether or not the nucleic acid detection step for the target nucleic acid containing the Wt detection sequence and the nucleic acid detection step for the target nucleic acid containing the Mut detection sequence are proper is made from one type of positive beads (i.e., Wt & Mut positive beads).

For example, the number of the Wt & Mut positive beads is counted. When the count result is equal to or larger than a third threshold value for the number of the Wt & Mut positive beads, it can be determined that the nucleic acid detection step is proper. When the count result for the number of the Wt & Mut positive beads is smaller than the third threshold value for the number of the Wt & Mut positive beads, it can be determined that the nucleic acid detection step is improper.

When it is determined that the nucleic acid detection step is improper, it is hypothesized that any one of the steps, including the nucleic acid sample preparation step, the compartment preparation step, the nucleic acid amplification step and the signal detection step, in the nucleic acid detection step is improper. It can be verified appropriately as to which step is improper by carrying out an additional test or the like, as mentioned above.

In the quality control method in which one type of Wt & Mut quality control polynucleotide is used, as is the case in the above-mentioned quality control method in which two types of quality control polynucleotides are used, a result on which it can be determined as to whether or not the result of the determination on the detection of a mutation in the target nucleic acid is reliable can be provided.

Hereinbelow, embodiments according to one aspect will be described in reference to the accompanied drawings. However, the below-mentioned description is illustrative only and not restrictive, and is not intended to limit the invention claimed in the appended claims in any way.

Embodiment 1

FIG. 1 shows a schematic diagram illustrating the nucleic acid detection step according to Embodiment 1. In Embodiment 1, a digital PCR is carried out while encapsulating beads in aqueous droplets in an oily phase to perform nucleic acid detection.

The material for the "beads" to be used in this embodiment is not particularly limited. Metallic particles, resin particles and the like can be used. Specific examples of the material for the metallic particles include gold, silver, copper, iron, aluminum, nickel, manganese, titanium and oxides of these metals. An alloy of any one of these materials may be used. Specific examples of the material for the resin particles include polystyrene and latex. The beads may be magnetized (wherein the beads are also referred to as "magnetic beads", hereinafter).

First, a nucleic acid sample containing a target nucleic acid, a quality control polynucleotide, beads each having, bound to the surface thereof, one of primers in a target nucleic acid amplification primer set, and other reagents necessary for nucleic acid amplification is prepared (FIG. 1(*i*)). The target nucleic acid to be used in Embodiment 1 contains one detection sequence (n=1), and the quality control polynucleotide contains two detection sequences (n=2). The nucleic acid sample that serves as an aqueous phase, an oily phase and an emulsifying agent are mixed together to form many aqueous droplets (compartments) in the oily phase by stirring or the like (FIG. 1(*ii*)). The aqueous droplets can be formed in an excess amount relative to the number of copies of the target nucleic acid and the quality control polynucleotide, and therefore one molecule of the quality control nucleic acid or one molecule of the target nucleic acid is contained in one aqueous droplet theoretically. The aqueous droplets can be formed in largely excessive number relative to the number of the beads, and therefore one bead is contained in one aqueous droplet theoretically. In general, tens of millions of droplets are formed in a digital PCR, and both one molecule of the target nucleic acid or one molecule of the quality control polynucleotide and one bead having the primer bound thereto are contained in about 0.1 to 1% of the droplets (FIGS. 1(*ii*)(*b*) and 1(*ii*)(*c*)). In each of other droplets, any one of these components is not generally contained (FIGS. 1(*ii*)(*a*1) to 1(*ii*)(*a*4)), and therefore nucleic acid amplification does not occur on these beads (FIGS. 1(*iii*)(*a*1) to 1(*iii*)(*a*4)). When the aqueous droplets are subjected to a PCR method, an extended amplification product is bound to the surface of a bead in an aqueous droplet containing one molecule of the target nucleic acid or one molecule of the quality control polynucleotide and one bead having the primer bound thereto (FIGS. 1(iii)(b) and 1(iii)(c)).

Subsequently, the aqueous droplets (compartments) are disrupted by a known means (e.g., the addition of a surfactant) (a disruption step), then a supernatant containing an amplification product that is not bound to beads and unreacted components is removed by centrifugation or the like (a B/F separation step), and then the beads are collected. A detection probe that is labeled with a fluorescent substance in advance is allowed to hybridize with the amplification product on the collected beads under stringent conditions. The B/F separation procedure is carried out again to remove unhybridized detection probes. Subsequently, each of the beads is irradiated with excitation light ($\lambda 1$), and a fluorescent signal ($\lambda 2$) originated from each of the beads is measured (a signal detection step). In this manner, a signal associated with the amplification product bound to the beads can be obtained. For the detection of the signal, a flow cytometer is used.

The number of detection probes that can hybridize on the beads to each of which an amplification product of the quality control polynucleotide is bound (FIG. 1(iii)(c)) is about twice larger than the number of detection probes that can hybridize on the beads to each of which an amplification product of the target nucleic acid is bound (FIG. 1(iii)(b)). As the result of this difference in the number of hybridized detection probes, a bead to which an amplification product of the quality control polynucleotide is bound can emit a fluorescent signal having an intensity about two times larger than that of a fluorescent signal emitted from a bead to which amplification product of the target nucleic acid is bound theoretically.

In this example, the preparation of the compartments is carried out by forming a microemulsion. The microemulsion can be formed by subjecting a mixture of a nucleic acid sample, an oily phase and an emulsifying agent to a stirring operation such as pipetting. In one embodiment, the microemulsion thus formed may contain, but not limited to, an aqueous phase at a proportion of 10 to 30% (v/v), the oily phase at a proportion of 60 to 85% (v/v) and the emulsifying agent at a proportion of 5 to 10% (v/v). A digital PCR involves a thermal cycle, and therefore the emulsifying agent is preferably a thermally stable one.

In Embodiment 1, in the nucleic acid amplification by a digital PCR, one of primers in the target nucleic acid amplification primer set is bound onto the beads. However, the number of types of the primer to be bound onto the beads in the nucleic acid amplification according to the embodiment is not limited to 1. In an alternative example of Embodiment 1, both of the primers in the target nucleic acid amplification primer set may be bound onto the beads.

In Embodiment 1, a detection probe which is labeled with a fluorescent dye in advance, can emit a signal by itself and can also emit a signal even after hybridization is used after the disruption step. This type of labeled detection probe can be used advantageously in embodiments in which a detection probe which is not hybridized with the amplification product can be removed by means of B/F separation.

In an alternative example of Embodiment 1, a probe which cannot emit a signal by itself and can emit a signal in its hybridized form, e.g., Molecular Beacon probe, may be used in the nucleic acid sample prior to the preparation of the compartments. According to this alternative example, it is also possible to detect a signal associated with the nucleic acid amplification from each of aqueous droplets (compartments) while retaining the compartments and without the need of disrupting the compartments.

It is determined as to whether or not the nucleic acid detection step is proper on the basis of the result of the detection of a signal coming from the beads to each of which an amplification product of the quality control polynucleotide is bound. As mentioned above, when it is determined that the nucleic acid detection step is proper, it can be determined that the result of the detection of the target nucleic acid is reliable. When it is determined that the nucleic acid detection step is improper, it can be determined that the result of the detection of the target nucleic acid is not reliable. According to Embodiment 1, the quality of the result of the detection of a nucleic acid can be controlled in this manner.

Embodiment 2

Figures 2A, 2B:
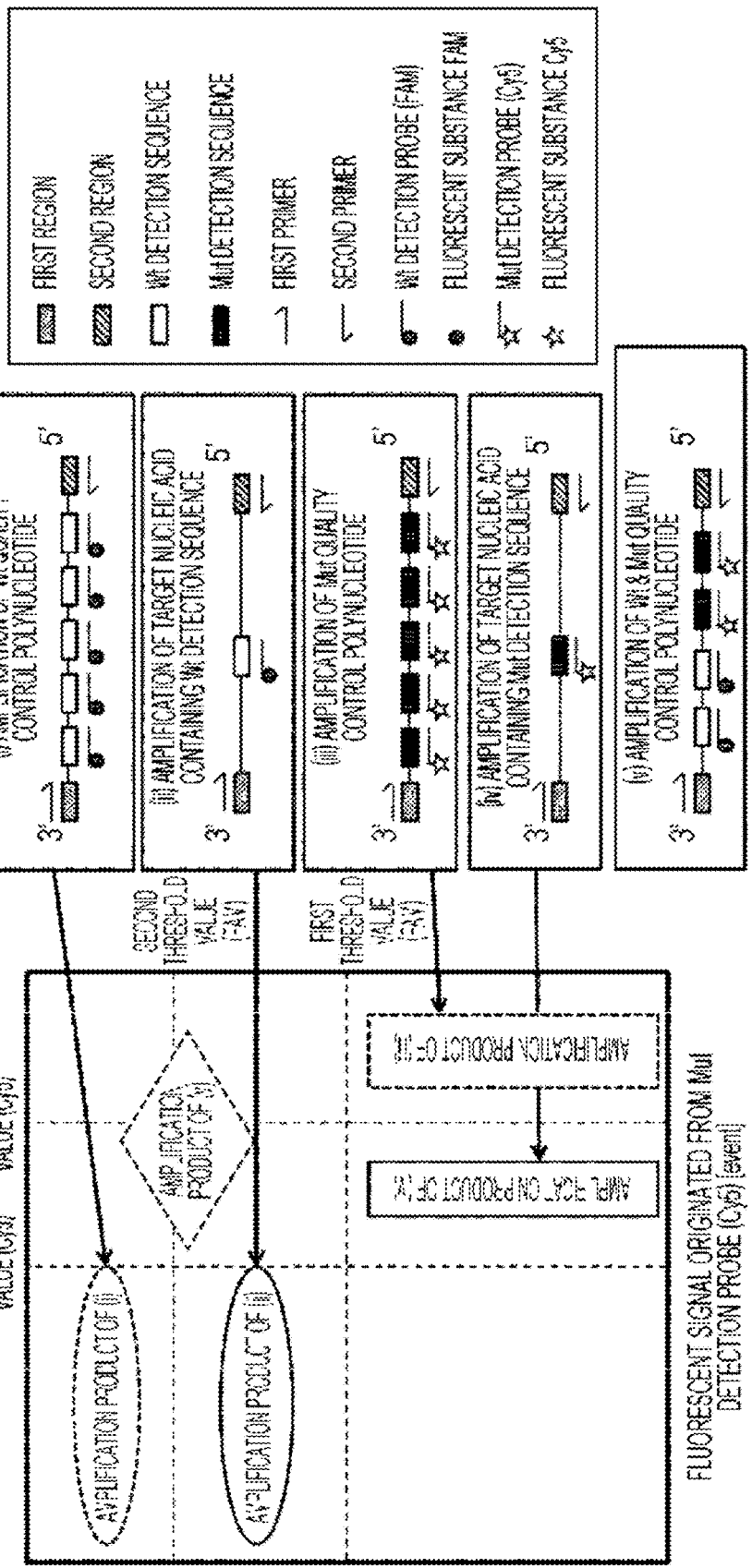
FIGS. 2A and 2B show schematic diagrams illustrating the 2D scattergram of detection signals and the types of nucleic acid amplification, respectively, in Embodiment 2.

Embodiment 2 relates to a method for controlling quality in the detection of a mutation in a target nucleic acid. FIG. 2A shows a schematic diagram illustrating a 2D scattergram of detection signals and FIG. 2B shows a schematic diagram illustrating the types of the nucleic acid amplification in Embodiment 2.

In Embodiment 2, a case where a sample containing a mutant form of a target nucleic acid and a wild-type of the target nucleic acid on a mixed state is used is described. As the quality control polynucleotide, two types of quality control polynucleotides, i.e., a quality control polynucleotide for detecting a Mut detection sequence (i.e., a Mut quality control polynucleotide) and a quality control polynucleotide for detecting a Wt detection sequence (i.e., a Wt quality control polynucleotide), are used. The Mut quality control polynucleotide contains five Mut detection sequences, and the Wt quality control polynucleotide contains five Wt detection sequences.

In Embodiment 2, the nucleic acid sample preparation step, the compartment preparation step and the nucleic acid amplification step are carried out in the same manner as in Embodiment 1. In the nucleic acid amplification step in Embodiment 2, the amplification of the Wt quality control polynucleotide (FIG. 2B(i)), the target nucleic acid containing the Wt detection sequence (FIG. 2B(ii)), the Mut quality control polynucleotide (FIG. 2B(iii)) and the target nucleic acid containing the Mut detection sequence (FIG. 2B(iv)) can be carried out using a target nucleic acid amplification primer set (a first primer and a second primer). As the result of the amplification, beads to each of which an amplification product of the Wt quality control polynucleotide is bound, beads to each of which an amplification product of the target nucleic acid containing the Wt detection sequence is bound, beads to each of which an amplification product of the Mut quality control polynucleotide is bound, and beads to each of which an amplification product of the target nucleic acid containing the Mut detection sequence is bound can be produced.

The beads are collected from the compartments in the same manner as in Embodiment 1. Detection probes are hybridized with the collected beads under stringent conditions. In Embodiment 2, a detection probe which can hybridize with a fluorescent substance Cy5-labeled Mut detection sequence (wherein the detection probe is also referred to as a "Mut detection probe (Cy5)", hereinafter) and a detection probe which can hybridize with a fluorescent substance FAM-labeled Wt detection sequence (wherein the detection probe is also referred to as a "Wt detection probe (FAM)", hereinafter) are used. The detection probes can emit different fluorescent signals from each other, because the detection probes are labeled with different fluorescent substances from each other. The detection probes are hybridized, then B/F separation is carried out, and then the detection probes which are not hybridized are removed. Signals coming from the beads are detected with a flow cytometer.

FIG. 2A shows a 2D scattergram in which the intensity of a fluorescent signal originated from a Mut detection probe (Cy5) is assigned to x-axis and the intensity of a fluorescent signal originated from a Wt detection probe (FAM) is assigned to y-axis.

The target nucleic acid containing the Mut detection sequence contains one (n=1) Mut detection sequence, and the Mut quality control polynucleotide contains five (n=5) Mut detection sequences. Therefore, one Mut detection probe (Cy5) can hybridize with a bead to which an amplification product of the target nucleic acid containing the Mut detection sequence is bound, and five Mut detection probes (Cy5) can hybridize with a bead to which an amplification product of the Mut quality control polynucleotide is bound. Consequently, the intensity of a Cy5-originated fluorescent signal which is obtained from a bead to which an amplification product of the Mut quality control polynucleotide is bound is larger than that obtained from a bead to which an amplification product of the target nucleic acid containing the Mut detection sequence is bound.

The hybridization of each of an amplification product of the target nucleic acid and an amplification product of the quality control polynucleotide with the detection probe is carried out under stringent conditions. Therefore, a FAM-originated fluorescent signal can be detected at a level lower than the detection limit or, if detected, an extremely low level of the fluorescent signal can be detected from each of an amplification product of the target nucleic acid containing the Mut detection sequence and an amplification product of the Mut quality control polynucleotide.

In FIG. 2A, the threshold value employed for the purpose of distinguishing a signal of an autofluorescence of a bead or the like from a fluorescent signal originated from a bead to which an amplification product of the target nucleic acid containing the Mut detection sequence is bound is shown as "first threshold value (Cy5)", and the threshold value employed for the purpose of distinguishing a fluorescent signal originated from a bead to which an amplification product of the target nucleic acid containing the Mut detection sequence is bound from a fluorescent signal originated from a bead to which an amplification product of the Mut quality control polynucleotide is bound is shown as "second threshold value (Cy5)".

A bead to which an amplification product of the target nucleic acid containing the Mut detection sequence is bound can be plotted in an area (iv) that is located between the first threshold value (Cy5) and the second threshold value (Cy5) and is below the below-mentioned first threshold value (FAM). A bead to which an amplification product of the Mut quality control polynucleotide is bound can be plotted in an area (iii) that is at the same level as or above the second threshold value (Cy5) and is below the below-mentioned first threshold value (FAM).

Similarly, the target nucleic acid containing the Wt detection sequence contains one (n=1) Wt detection sequence, and the Wt quality control polynucleotide contains five (n=5) Wt detection sequences. Therefore, one Wt detection probe (FAM) can hybridize to a bead to which an amplification product of the target nucleic acid containing the Wt detection sequence is bound, and five Wt detection probes (FAM) can hybridize to a bead to which an amplification product of the Wt quality control polynucleotide is bound. The hybridization of an amplification product of each of the nucleic acids with the detection probe is carried out under stringent conditions. Consequently, the intensity of a FAM-originated fluorescent signal which is obtained from a bead to which an amplification product of the Wt quality control polynucleotide is bound is larger than that obtained from a bead to which an amplification product of the target nucleic acid containing the Wt detection sequence is bound. A Cy5-originated fluorescent signal can be detected at a level lower than the detection limit or, if detected, an extremely low level of the fluorescent signal can be detected from each of the amplification products.

In FIG. 2A, the threshold value employed for the purpose of distinguishing a signal of an autofluorescence of a bead or the like from a fluorescent signal originated from a bead to which an amplification product of the target nucleic acid containing the Wt detection sequence is bound is shown as "first threshold value (FAM)", and the threshold value employed for the purpose of distinguishing a fluorescent signal originated from a bead to which an amplification product of the target nucleic acid containing the Wt detection sequence is bound from a fluorescent signal originated from a bead to which an amplification product of the Wt quality control polynucleotide is bound is shown as "second threshold value (FAM)".

A bead to which an amplification product of the target nucleic acid containing the Wt detection sequence is bound can be plotted in an area (ii) that is located between the first threshold value (FAM) and the second threshold value (FAM) and is below the first threshold value (Cy5). A bead to which an amplification product of the Wt quality control polynucleotide is bound can be plotted in an area (i) that is at the same level as or above the second threshold value (FAM) and is below the first threshold value (Cy5).

In the determination step in Embodiment 2, the presence or absence of a mutation is determined. For example, the determination can be made by employing, as a measure, a matter that how much concentration (how many number of copes) of the target nucleic acid, among the total concentration (total number of copies) of the target nucleic acid containing the Mut detection sequence. When dots exist in both the areas (ii) and (iv) where beads to each of which an amplification product of the target nucleic acid is bound can be plotted, the ratio of the number of dots in the area (iv) to the total number of dots in the areas (ii) and (iv) (=(the number of dots in the area (iv))/[(the number of dots in the area (ii))+(the number of dots in the area (iv))]) is calculated. When the ratio is equal to or larger than a predetermined threshold value, it can be determined that a mutation occurs.

In the determination step, the determination as to whether or not the nucleic acid detection step is proper is made.

In Embodiment 2, when the number of dots in the area (iii) where beads to each of which an amplification product of the Mut quality control polynucleotide is bound can be plotted is equal to or larger than a predetermined threshold value, it can be determined that the nucleic acid detection step for the target nucleic acid containing the Mut detection sequence is proper. This determination result suggests that the result of the determination on the presence or absence of a mutation in the target nucleic acid is reliable.

In Embodiment 2, a signal coming from the wild-type detection probe and originated from the Wt quality control polynucleotide can also be detected. When the number of dots in the area (i) where beads to each of which an amplification product of the Wt quality control polynucleotide is bound can be plotted is equal to or larger than a predetermined threshold value, it can be determined that the nucleic acid detection step for the target nucleic acid containing the Wt detection sequence is proper. This result of the determination with respect to the area (i) can give reliability to the result of the above-mentioned determination with respect to the area (iii) (i.e., the result that the nucleic acid detection step for the target nucleic acid containing the Mut detection sequence is proper).

As mentioned above, when two types of quality control polynucleotides are used, the reliability of the quality control for a target nucleic acid can be further improved compared with the case where only one type of quality control polynucleotide is used. As a result, the quality in the detection of a mutation in the target nucleic acid can also be further improved.

When the number of dots in the area (iii) is smaller than a predetermined threshold value, it is determined that the nucleic acid detection step for the target nucleic acid containing the Mut detection sequence is improper. This detection result suggests that the result of the determination on the presence or absence of a mutation in the target nucleic acid is not reliable. In this case, an additional test may be carried out, if necessary, on the basis of the determination result "the nucleic acid detection step is improper", in order to verify as to which step in the nucleic acid detection step is improper. When the number of dots in the area (i) is equal to or larger than a predetermined threshold value, it is determined that the nucleic acid detection step for the target nucleic acid containing the Wt detection sequence is proper. In this case, in the additional test, it can be hypothesized that the signal detection step in the nucleic acid detection step is improper, as mentioned above.

As mentioned above, the use of two types of quality control polynucleotides is advantageous compared with the use of only one type of quality control polynucleotide, because additional information can be obtained with respect to which step in the nucleic acid detection step for the target nucleic acid is improper.

Alternative Example of Embodiment 2

In Embodiment 2, two types of detection probes (i.e., a mutant detection probe and a wild-type detection probe) and two types of quality control polynucleotides (i.e., a Mut quality control polynucleotide and a Wt quality control polynucleotide) are used. In this alternative example, the method for controlling quality in the detection of a mutation in a target nucleic acid using one type of quality control polynucleotide and the above-mentioned two types of detection probes is described.

In this alternative example, a polynucleotide containing two Wt detection sequences and two Mut detection sequences (wherein the polypeptide is also referred to as a "Wt & Mut quality control polynucleotide", hereinafter) is used as the quality control polynucleotide. As is the case in Embodiment 2, the target nucleic acid contains one Mut detection sequence or one Wt detection sequence. As is the case in Embodiment 2, the Wt detection probe (FAM) and the Mut detection probe (Cy5) are used as the detection probes. In this alternative example, the nucleic acid detection step is carried out in the same manner as in Embodiment 2.

In FIG. 2A, as is the case in Embodiment 2, beads to each of which an amplification product of the target nucleic acid containing the Wt detection sequence is bound are plotted in the area (ii), and beads to each of which an amplification product of the target nucleic acid containing the Mut detection sequence is bound are plotted in the area (iv).

Two Wt detection probes (FAM) and two Mut detection probes (Cy5) can hybridize with beads to each of which an amplification product of the Wt & Mut quality control polynucleotide is bound. Therefore, the intensity of a FAM-originated fluorescent signal which is obtained from the beads to each of which an amplification product of the Wt & Mut quality control polynucleotide is bound is larger than that obtained from beads to each of which an amplification product of the target nucleic acid containing the Wt detection sequence is bound. The intensity of a Cy5-originated fluorescent signal which is obtained from the aforementioned beads is larger than that obtained from beads to each of which an amplification product of the target nucleic acid containing the Mut detection sequence is bound.

In this alternative example, a second threshold value is used in order to distinguish the intensity of a fluorescent signal originated from the detection probe for the amplification product of the target nucleic acid from the intensity of a fluorescent signal originated from the detection probe for the amplification product of the Wt & Mut quality control polynucleotide. The second threshold value for a signal originated from the Mut detection probe (Cy5) refers to as a "second threshold value (Cy5)", and the second threshold value for a signal originated from the Wt detection probe (FAM) refers to as a "second threshold value (FAM)" (these second threshold values are not shown in FIG. 2A).

Beads to each of which an amplification product of the Wt & Mut quality control polynucleotide is bound can be plotted in an area that is located at the same level as or above the second threshold value (FAM) and at the same level as or above the second threshold value (Cy5) (FIG. 2A, area (v)).

With respect to the determination on the presence or absence of a mutation in this alternative example, as is the case in Embodiment 2, the ratio of the number of dots in the area (iv) to the total number of dots in the areas (ii) and (iv) (=(the number of dots in the area (iv))/[(the number of dots in the area (ii))+(the number of dots in the area (iv))]) is calculated, and it can be determined that a mutation occurs when the ratio is equal to or larger than a predetermined threshold value.

With respect to the determination as to whether or not the nucleic acid detection step is proper in this alternative example, it can be determined that the nucleic acid detection step in the detection of a mutation in the target nucleic acid is improper when the number of dots in the area (v) where beads to each of which an amplification product of the Wt & Mut quality control polynucleotide is bound can be plotted is smaller than a predetermined threshold value. On the other hand, it can be determined that the nucleic acid detection step in the detection of a mutation in the target nucleic acid is proper when the number of dots in the area (v) is equal to or larger than a predetermined threshold value. As mentioned in Embodiment 2, the control of quality in the detection of a mutation in the target nucleic acid can be achieved on the basis of the results of the determination.

Embodiment 3

Figure 3:
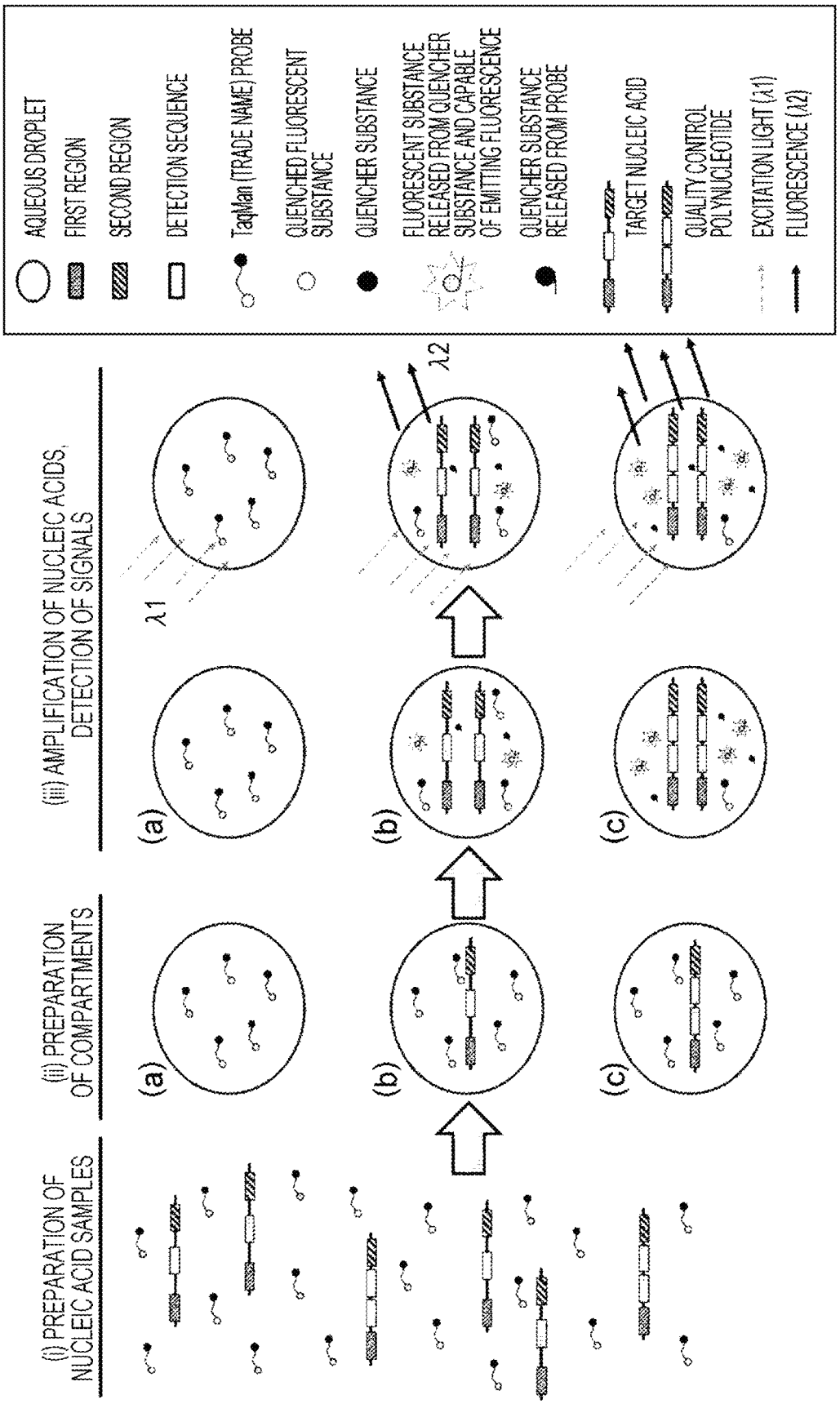
FIG. 3 shows a schematic diagram illustrating the nucleic acid detection step in Embodiment 3.

FIG. 3 shows a schematic diagram illustrating the nucleic acid detection step in Embodiment 3. In Embodiment 3, unlike Embodiment 1, an example is shown, in which the nucleic acid amplification is carried out by a droplet-type digital PCR and then a signal is detected from each of compartments without disrupting the compartments.

In Embodiment 3, a nucleic acid sample is prepared, which contains a target nucleic acid, a quality control polynucleotide, a TaqMan (trade name) probe which can hybridize with a detection sequence (i.e., a detection probe), a polymerase having a 5'→3' exonuclease activity (not shown) and other reagents needed for the nucleic acid amplification (FIG. 3(i)). With respect to the target nucleic acid and the quality control polynucleotide used in Embodiment 3, as is the case in Embodiment 1, the target nucleic acid contains one (n=1) detection sequence and the quality control polynucleotide contains two (n=2) detection sequences.

In the compartment preparation step, aqueous droplets (compartments) in an oily phase are formed in the same manner as in Embodiment 1 (FIG. 3(ii)). Among many aqueous droplets thus formed, aqueous droplets each containing one molecule of the target nucleic acid or the quality control polynucleotide and a plurality of TaqMan (trade name) probes are prepared (FIGS. 3(ii)(b) and 3(ii)(c)). The aqueous droplets are subjected to a PCR method. In aqueous droplets each containing one molecule of the target nucleic acid or the quality control polynucleotide, an amplification product of the nucleic acid is produced (FIGS. 3(iii)(b) and 3(iii)(c)). In other aqueous droplets, the target nucleic acid or the quality control polynucleotide is not contained normally (FIG. 3(ii)(a)), and therefore nucleic acid amplification cannot occur when a PCR method is performed (FIG. 3(iii)(a)). During the nucleic acid amplification step, the TaqMan (trade name) probe is digested by the action of the 5'→3' exonuclease activity of the polymerase. A fluorescent substance is released from a quencher substance upon the digestion of the TaqMan (trade name) probe, and the released fluorescent substance is made into a fluorescence-emittable state. With respect to the target nucleic acid, one molecule of the TaqMan (trade name) probe can be digested during the amplification of one molecule of a single strand per one round of nucleic acid amplification. As a result, one molecule of the fluorescent substance can be converted into a fluorescence-emittable state. With respect to the quality control polynucleotide, two molecules of the TaqMan (trade name) probe can be digested during the amplification of one molecule of a strand per one round of nucleic acid amplification. As a result, two molecules of the fluorescent substance can be converted into a fluorescence-emittable state.

In the signal detection step, each of the aqueous droplets are irradiated with excitation light ($\lambda 1$), and a fluorescent signal ($\lambda 2$) coming from each of the aqueous droplets is measured. The intensity of the measured fluorescent signal can reflect the number of fluorescence-emittable fluorescent substances. It is considered that the number of fluorescence-emittable fluorescent substances which can be present in each of the aqueous droplets each containing one molecule of the quality control polynucleotide is twice larger than the number of fluorescence-emittable fluorescent substances which can be present in each of the aqueous droplets each containing one molecule of the target nucleic acid. Due to this difference in the number of fluorescence-emittable fluorescent substances, the intensity of a fluorescent signal coming from the aqueous droplets each containing one molecule of the quality control polynucleotide can be theoretically about twice larger than that coming from the aqueous droplets each containing one molecule of the target nucleic acid.

The determination as to whether or not the nucleic acid detection step is proper is made on the basis of the result of the detection of a signal coming from a compartment (droplet) in which amplification product of the quality control polynucleotide are produced. As mentioned above, when it is determined that the nucleic acid detection step is proper, it can be determined that the result of the detection of the target nucleic acid is reliable. When it is determined that the nucleic acid detection step is improper, it can be determined that the result of the detection of the target nucleic acid is not reliable. According to Embodiment 3, the quality of the result of the detection of a nucleic acid can be controlled in this manner.

Embodiment 4

Figure 4:
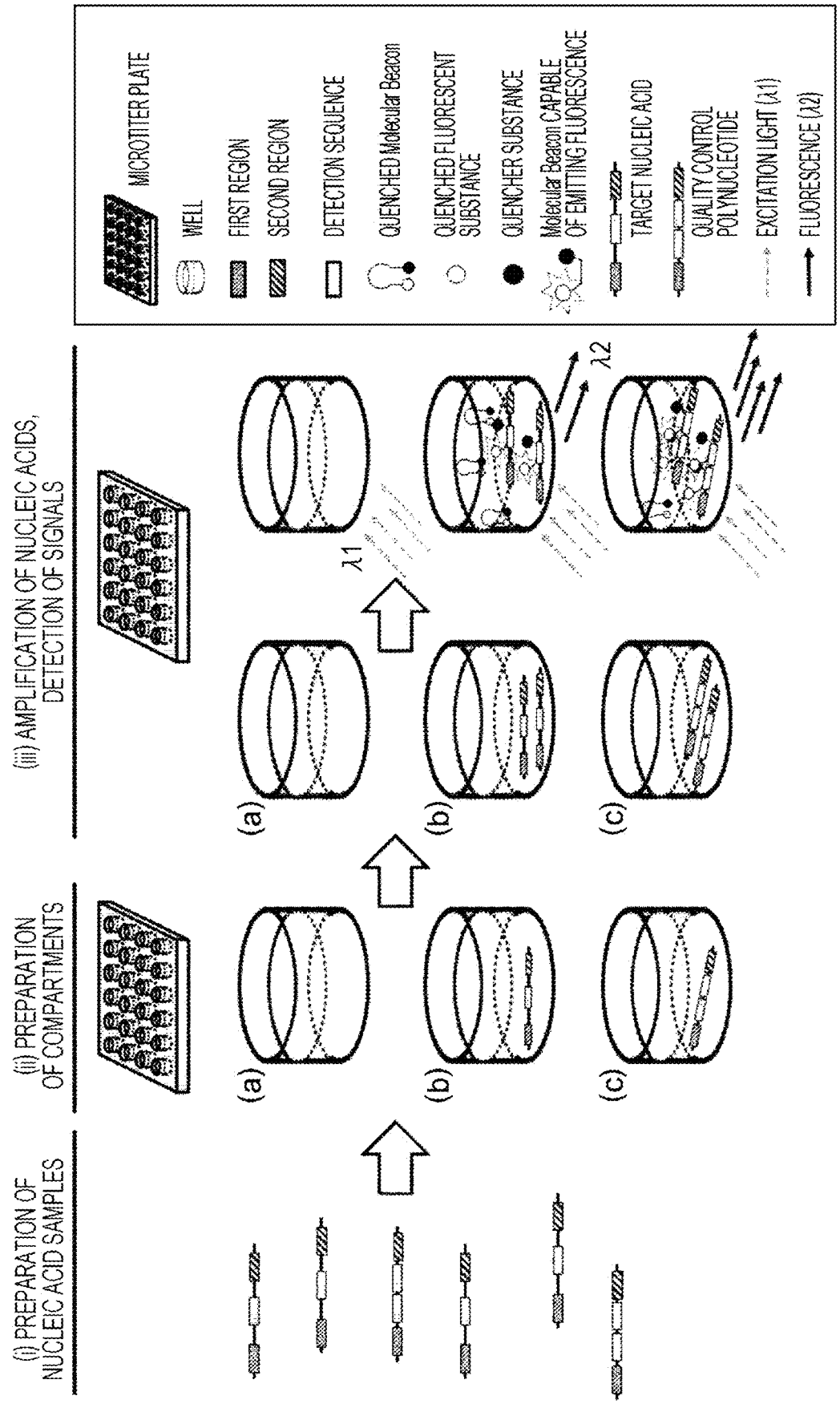
FIG. 4 shows a schematic diagram illustrating the nucleic acid detection step in Embodiment 4.

FIG. 4 shows a schematic diagram illustrating the nucleic acid detection step in Embodiment 4. In Embodiment 4, unlike Embodiment 3, an example in which nucleic acid amplification is carried out by a well-type digital PCR is described.

In Embodiment 4, a nucleic acid sample is prepared, which contains a target nucleic acid, a quality control polynucleotide and other reagents needed for nucleic acid amplification (FIG. 4(i)). With respect to the target nucleic acid and the quality control polynucleotide used in Embodiment 4, as is the case in Embodiment 3, the target nucleic acid contains one (n=1) detection sequence and the quality control polynucleotide contains two (n=2) detection sequences.

In the compartment preparation step, unlike Embodiment 3, the nucleic acid sample is dispensed into multiple wells (compartments) in a microtiter plate. Among the multiple wells, wells each containing one molecule of the target nucleic acid or the quality control polynucleotide are prepared (FIGS. 4(ii)(b) and 4(ii)(c)). The nucleic acid sample dispensed in the wells is subjected to a PCR method. In wells each containing one molecule of the target nucleic acid or the quality control polynucleotide, an amplification product of the nucleic acid is produced (FIGS. 4(iii)(b) and 4(iii)(c)). In other wells, the target nucleic acid or the quality control polynucleotide is not contained normally (FIG. 4(ii)(a)), and therefore nucleic acid amplification cannot occur when a PCR method is performed (FIG. 4(iii)(a)).

In Embodiment 4, after the nucleic acid amplification, a detection probe which cannot emit a signal by itself but can emit a signal upon hybridization, e.g., Molecular Beacon, is added to the wells. When an amplification product is present, the detection probe is allowed to hybridize with the amplification product under stringent conditions. Molecular Beacon probe is an oligonucleotide which is labeled with a fluorescent substance at one terminal thereof and also labeled with a quencher substance at the other terminal thereof, contains a sequence hybridizable with the detection sequence and can have a hair-pin-shaped secondary structure. Molecular Beacon probe loses its hair-pin-shaped secondary structure upon the hybridization with the detection sequence to form an extended structure. As a result, the labeling fluorescent substance can be converted into a fluorescence-emittable state. The target nucleic acid contains one (n=1) detection sequence, and therefore one molecule of Molecular Beacon probe can hybridize with the target nucleic acid. The quality control polynucleotide contains two (n=2) detection sequences, and therefore two molecules of Molecular Beacon probe can hybridize with the quality control polynucleotide.

In the signal detection step, the individual wells are irradiated with excitation light (λ1), and a fluorescent signal (λ2) coming from each of the wells is measured. For the detection of a fluorescent signal, a microtiter plate reader is used. The intensity of the measured fluorescent signal can reflect the number of Molecular Beacon probes which have hybridized with the amplification product (i.e., the number of fluorescence-emittable fluorescent substances). It is considered that the number of Molecular Beacon probes which have hybridized with the amplification product in wells each containing one molecule of the quality control polynucleotide is about twice larger than that in wells each containing one molecule of the target nucleic acid. Due to this difference in the number of hybridized Molecular Beacon probes, the intensity of a fluorescent signal coming from the wells each containing one molecule of the quality control polynucleotide can be theoretically about twice larger than that originated from the wells each containing one molecule of the target nucleic acid.

The determination as to whether or not the nucleic acid detection step is proper is made on the basis of the result of the detection of a signal originated from a compartment (well) in which an amplification product of the quality control polynucleotide is produced. As mentioned above, when it is determined that the nucleic acid detection step is proper, it can be determined that the result of the detection of the target nucleic acid is reliable. When it is determined that the nucleic acid detection step is improper, it can be determined that the result of the detection of the target nucleic acid is not reliable. According to Embodiment 4, the quality of the result of the detection of a nucleic acid can be controlled in this manner.

In Embodiment 4, Molecular Beacon probe is used as the detection probe. However, the mode of the practice is not limited thereto. For example, in the nucleic acid preparation in Embodiment 4, it is also possible to prepare a nucleic acid sample which additionally contains TaqMan (trade name) probe and the polymerase having a 5'→3' exonuclease activity both used in Embodiment 3, then dispense the prepared nucleic acid sample into wells as mentioned in Embodiment 4 (compartment preparation), and then perform nucleic acid amplification. In the signal detection step, a fluorescent signal originated from the fluorescent substance that is separated from the quencher substance during the nucleic acid amplification and becomes in a fluorescence-emittable state can be detected.

It is also possible to use beads each having a primer immobilized thereonto. In this case, it is possible to place one bead per one well in the microtiter plate and carry out the nucleic acid amplification and the detection of a signal in the same manner as mentioned above.

[Reagent for Use in Quality Control]

A second aspect provides a reagent for use in quality control, which contains a quality control polynucleotide. The characteristic properties described in association with the quality control polynucleotide in the first aspect can apply to the quality control polynucleotide contained in the reagent.

[Reagent Kit for Use in Quality Control]

Figure 10:
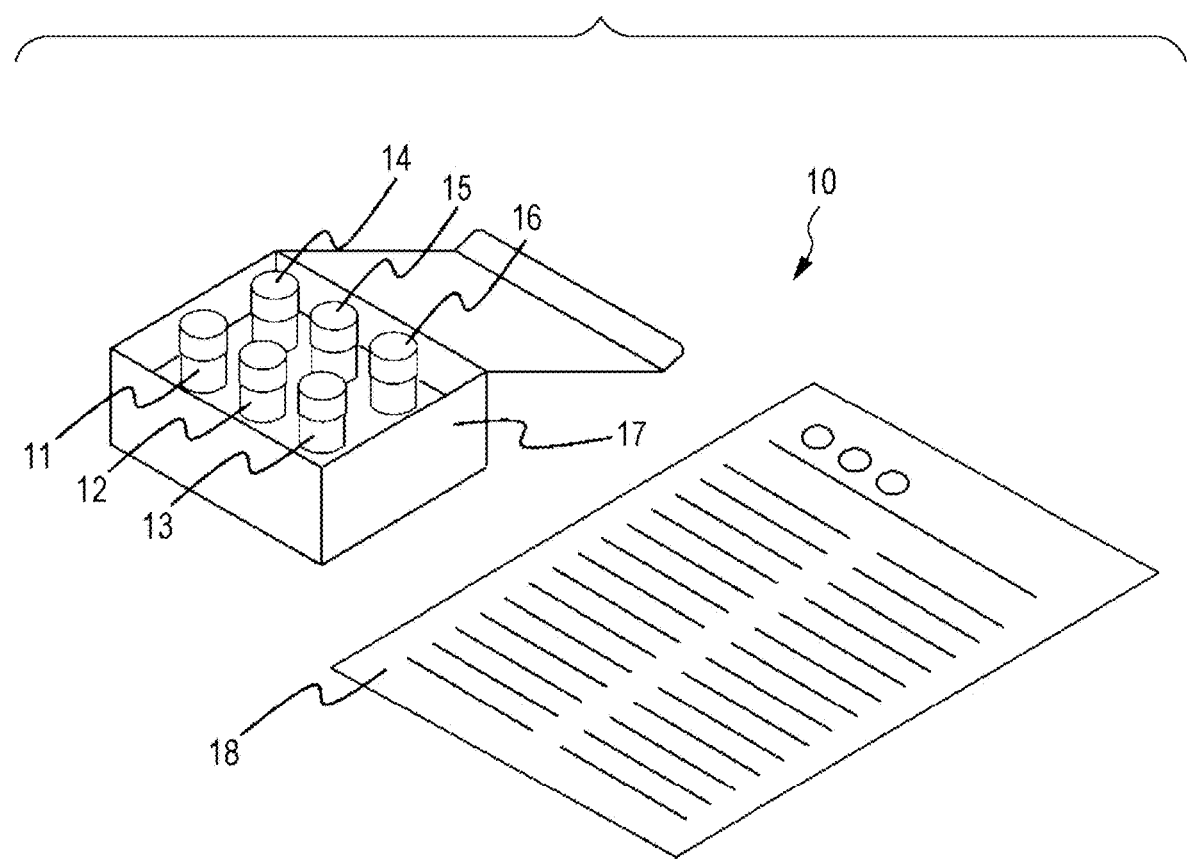
FIG. 10 shows a schematic diagram illustrating a reagent for use in quality control according to one embodiment.

In one embodiment of the third aspect, a reagent kit for use in quality control includes a reagent container in which a quality control polynucleotide is contained. A reagent container in which a necessary reagent such as a primer set, a detection probe, a polymerase, dNTPs or the like is included may be included in the kit appropriately. A package leaflet on which the usage of the reagent and the like are mentioned may also be included. FIG. 10 shows a schematic diagram illustrating one example of the reagent kit for use in quality control according to this embodiment. The kit includes: a reagent container (11) in which a quality control polynucleotide is contained; a reagent container (12) in which a first primer is contained; a reagent container (13) in which a second primer is contained; a reagent container (14) in which a detection probe is contained; a reagent container (15) in which a polymerase is contained; a reagent container (16) in which nucleoside triphosphates (dNTPs) are contained; and a package leaflet (18). The reagent containers (11) to (16) and the package leaflet (18) are included in a case (17).

In the kit illustrated in FIG. 10, reagents are contained in different containers from one another. However, reagents which can co-exist together without causing any trouble in nucleic acid amplification or signal detection can be contained together in a single container. The selection as to which reagents are to co-exist can be made appropriately by a person skilled in the art. For example, a first primer, a second primer and dNTPs can be contained in a single container.

The characteristic properties mentioned in association with the quality control polynucleotide and the detection probe in the present specification can apply to the quality control polynucleotide and the detection probe used in the kit.

One embodiment relates to a use of the quality control polynucleotide for producing the reagent for use in quality control or the reagent kit for use in quality control. The characteristic properties of the reagent for use in quality control, the reagent kit for use in quality control and the quality control polynucleotide are as mentioned above.

One embodiment relates to a use of the quality control polynucleotide, the reagent for use in quality control or the reagent kit for use in quality control in the nucleic acid amplification quality control method according to the first aspect. Another embodiment relates to the quality control polynucleotide, the reagent for use in quality control and the reagent kit for use in quality control for use in the nucleic acid amplification quality control method according to the first aspect. The characteristic properties of the reagent for use in quality control, the reagent kit for use in quality control, the quality control polynucleotide and the quality control method are as mentioned above.

Hereinbelow, specific examples will be described. However, it should be understood that these specific examples illustrate only preferred embodiments and do not limit the invention described in the appended claims in any way. It is construed that equivalents, alterations, modifications or variations recognized readily from the specific embodiments, materials, compositions and methods described in the specification are included within the scope of the disclosure.

EXAMPLES

In Examples, the following reagents, devices and analysis softwares were used.

<Reagents>

Phusion II Hot-start High Fidelity DNA polymerase (Thermo Scientific)

Platinum Taq DNA polymerase (Life Technologies)

Quanat PicoGreen dsDNA Assay Kit (Life Technologies)

Deoxynucleoside triphosphates (10 mmol/L for each, Life Technologies)

10×PCR buffer (670 mmol/L Tris-HCl pH 8.8, 166 mmol/L ammonium sulfide, 100 mmol/L 2-mercaptoethanol, 11.7 mmol/L magnesium chloride)

EmulsiFIRE (7% (v/v) ABIL WE09, 20% (v/v) mineral oil, 73% (v/v) Tegosoft DEC)

TE buffer pH 7.5 (10 mmol/L Tris-HCl pH 7.0, 1 mmol/L ethylenediaminetetraacetic acid)

Breaking buffer (10 mmol/L Tris-HCl pH 7.5, 1% Triton X-100, 1% sodium dodecyl sulfate, 100 mmol/L sodium chloride, 1 mmol/L ethylenediaminetetraacetic acid)

0.1 mol/L sodium hydroxide

TK buffer (20 mmol/L Tris-HCl pH 8.4, 50 mmol/L potassium chloride)

5×hybridization buffer (75 mmol/L Tris-HCl pH 9.5, 33.5 mmol/L magnesium chloride, 25% formamide)

Dynabeads MyOne Streptoavidin C1 (Dynal)

Stainless beads (5 mm)<device>

Veriti thermal cycler (Applied Biosystems)

BD Accuri C6 flow cytometer (Beckton Dickinson)

<analysis software>

FlowJo (FlowJo)

[Example 1]<Preparation of KRAS Amplification Sample DNA>

A DNA sample which contained a plasmid carrying a gene sequence for wild-type human KRAS and a plasmid carrying a gene sequence for mutant human KRAS c.38G>A at a mixing ratio of 99:1 was prepared. The prepared DNA sample was amplified by a PCR method using Phusion II High Fidelity DNA polymerase (Thermo Scientific) and a primer set shown in Table 1. The PCR reaction was carried out using Veritithermal cycler (Applied Biosystems). In the following experiments, Veritithermal cycler was also used for the implementation of a PCR reaction.

TABLE 1

| Primer | SEQ ID NO: | Sequence 5'→3' |
|---|---|---|
| Reverse primer 1 | SEQ ID NO: 3 | GCTGGAGCTCTGCAGCTATGACTGAA TATAAACTTGTGGTAGTTG |
| Forward primer 2 | SEQ ID NO: 4 | TCCCGCGAAATTAATACGACCATATT CGTCCACAAAATGATTC |

In Table 2, exon 2 in a wild-type human KRAS gene (which is represented by SEQ ID NO: 8) and exon 2 in a mutant human KRAS c.38G>A gene (which is represented by SEQ ID NO: 9) are shown. Sequence segments written in capital letters in the sequences shown in Table 2 were amplified by the above-mentioned PCR using the primer sets shown in Table 1. In the sequences shown in Table 2, underlined regions show the below-mentioned detection sequences, and regions enclosed in boxes show regions with which the below-mentioned common probes can hybridize.

TABLE 2

| Gene | SEQ ID NO: | Sequence 5' → 3' |
|---|---|---|
| Exon 2 in wild-type human KRAS gene | SEQ ID NO: 8 | ctctattgttggatCATATTCGTCCACAAAATGATTCTGAATTAG CTGTATCGTCAAGGCACTCTTGCCTACGCCACCAGCTCCAA CTACCACAAGTTTATATTCAGTCAttttcagcaggc |
| Exon 2 in mutant human KRAS c.38G>A gene | SEQ ID NO: 9 | ctctattgttggatCATATTCGTCCACAAAATGATTCTGAATTAG CTGTATCGTCAAGGCACTCTTGCCTACGTCACCAGCTCCA ACTACCACAAGTTTATATTCAGTCAttttcagcaggc |

Each of the amplification products thus produced was quantitated with PicoGreen fluorescence intercalator (Quant-lt PicoGreen dsDNA Assay Kit (Life Technologies)). Each of the amplification products is referred to as "KRAS amplification sample DNA", hereinafter.

<Preparation of Quality Control Polynucleotide>

As the quality control polynucleotides, single-stranded DNA molecules respectively containing the sequences represented by SEQ ID NO: 10 to SEQ ID NO: 15 were prepared. The single-stranded DNA molecules were chemically synthesized by a β-cyanoethyl phosphoramidite method. Each of the synthesized DNA molecules was amplified by a PCR method using Phusion II High Fidelity DNA polymerase (Thermo Scientific) and a primer set shown in Table 1. Each of the amplification products was purified, and then quantitated by an ultraviolet ray absorption method. The amplification products were named as shown in Table 3. Each of the quality control polynucleotides contained a detection sequence in wild-type (Wt) human KRAS gene sequence or a detection sequence in the mutant (Mut) human KRAS gene sequence (wherein the detection sequences are referred to as a "Wt detection sequence" and a "Mut detection sequence", respectively) in the number of sequences shown in Table 3. The Wt detection sequence is an underlined sequence segment in the sequence represented by SEQ ID NO: 8 shown in Table 2, and the Mut detection sequence is an underlined sequence segment in the sequence represented by SEQ ID NO: 9 in Table 2. In Table 3, the detection sequences segments are underlined.

TABLE 3

| Name of polynucleotide | SEQ ID NO: | Sequence 5'→3' | Number of Wt detection sequences | Number of Mut detection sequences |
|---|---|---|---|---|
| Quality control polynucleotide (Wt, n = 5) | SEQ ID NO: 10 | TCATATTCGTCCACAAAATGATTCAGAT<u>GCCTACGCCACCAGC</u>TATC<br>AGCCATACGCCACCAGCTCAGT<u>GCCTACGCCACCAGC</u>TACTA<u>GCCTA</u><br><u>CGCCACCAGC</u>TATGAGCCTACGCCACCAGCTACGATGCAACTACCAC<br>AAGTTTATATTCAGTCAT | 5 | — |
| Quality control polynucleotide (Wt, n = 4) | SEQ ID NO: 11 | TCATATTCGTCCACAAAATGATTCAGAT<u>GCCTACGCCACCAGC</u>TATC<br>AGCCTACGCCACCAGCTCAGT<u>GCCTACGCCACCAGC</u>TACTA<u>GCCTAC</u><br><u>GCCACCAGC</u>TATGAACCTCTATTGTTGGATACGATGCAACTACCACA<br>AGTTTATATTCAGTCAT | 4 | — |
| Quality control polynucleotide (Wt, n = 3) | SEQ ID NO: 12 | TCATATTCGTCCACAAAATGATTCAGAT<u>GCCTACGCCACCAGC</u>TATC<br>AGCCTACGCCACCAGCTCAGT<u>GCCTACGCCACCAGC</u>TACTATATTAA<br>AACAAGATTTATGAACCTCTATTGTTGGATACGATGCAACTACCACA<br>AGTTTATATTCAGTCAT | 3 | — |
| Quality control polynucleotide (Wt, n = 2) | SEQ ID NO: 13 | TCATATTCGTCCACAAAATGATTCAGAT<u>GCCTACGCCACCAGC</u>TATC<br>AGCCTACGCCACCAGCTCAGTGCCACCAGTAATATGCAACTATATTAA<br>AACAAGATTTATGAACCTCTATTGTTGGATACGATGCAACTACCACA<br>AGTTTATATTCAGTCAT | 2 | — |
| Quality control polynucleotide (Mut, n = 5) | SEQ ID NO: 14 | TCATATTCGTCCACAAAATGATTCT<u>GCCTACGTCACCAGC</u>TATCAGC<br>CTACGTCACCAGCTCAGT<u>GCCTACGTCACCAGC</u>TACTA<u>GCCTACGTC</u><br><u>ACCAGC</u>TATGAG<u>CCTACGTCACCAGC</u>TCCAACTACCACAAGTTTATA<br>TTCAGTCAT | - | 5 |
| Quality control polynucleotide (Wt, n = 6) | SEQ ID NO: 15 | TCATATTCGTCCACAAAATGATTCT<u>GCCTACGCCACCAGC</u>TA<u>GCCTA</u><br>CGCCACCAGCTT<u>GCCTACGCCACCAGC</u>T<u>GGCCTACGCCACCAGC</u>TCG<br>CCTACGCCACCAGCTA<u>GCCTACGCCACCAGC</u>TCCAACTACCACAAGT<br>TTATATTCAGTCAT | 6 | — |

<Preparation of Primer-Bound Magnetic Beads>

A single-stranded DNA molecule having the sequence represented by SEQ ID NO: 1 (5'-TCCCGCGAAAT-TAATACGAC-3') was prepared. A biotin dimer was bound to the 5'-terminal of the single-stranded DNA molecule to prepare a biotinylated primer. The biotinylated primer was added to streptavidin-modified magnetic beads (Dynabeads MyOne Streptoavidin C1 (Dynal)) to bind the primer to the magnetic beads, thereby preparing primer-bound magnetic beads. The primer-bound magnetic beads were washed to remove unbound biotinylated primer.

<BEAMing Method>

Nucleic acid amplification was carried out by a BEAMing (Beads, Emulsions, Amplification and Magnetics) method which is a droplet-type digital PCR using magnetic beads. The following PCR reaction solutions were prepared (wherein the concentrations are expressed as final concentrations).

Subsequently, 64 μL of EmulsiFIRE (7% (v/v) ABIL WE09, 20% (v/v) mineral oil, 73% (v/v) Tegosoft DEC) was added to each of the PCR reaction solutions. Each of the solutions was subjected to inversion mixing in the presence of stainless beads (5 mm). In this manner, emulsions were produced. The emulsions were subjected to a PCR reaction under the following conditions.

| Step | Thermal denaturation | Annealing | Extension | Number of cycles |
|---|---|---|---|---|
| 1 | 94° C., 2 min. | | | |
| 2 | 98° C., 15 sec. | 64° C., 45 sec. | 72° C., 75 sec. | 3 |
| 3 | 98° C., 15 sec. | 61° C., 45 sec. | 72° C., 75 sec. | 3 |
| 4 | 98° C., 15 sec. | 58° C., 45 sec. | 72° C., 75 sec. | 3 |
| 5 | 98° C., 15 sec. | 57° C., 45 sec. | 72° C., 75 sec. | 50 |

```
KRAS amplification sample DNA                    1 x 10^7 copies

Quality control polynucleotide (Wt, n = 5)       100,000 copies 10 x PCR buffer                                  1.6 µl Deoxynucleoside triphosphates (dNTPs)            0.2 mmol/L Forward primer 5                                 50 fmol/L
(SEQ ID NO: 1: 5'-TCCCGCGAAATTAATACGAC-3')

Reverse primer 6                                 8 pmol/L
(SEQ ID NO: 2 : 5'-GCTGGAGCTCTGCAGCTA-3')

Primer-bound magnetic beads                      0.64 µL

Taq DNA polymerase (Life Technologies)           5 units

Volume                                           16 µl
```

The primer bound to the primer-bound magnetic beads had the same sequence as the sequence for the forward primer 5 (the sequence represented by SEQ ID NO: 1) used in the PCR reaction solution. By the PCR, for example, a complementary sequence to the primer bound to the magnetic beads was extended from the primer using a KRAS amplification sample DNA molecule hybridized with the primer as a template. In this manner, magnetic beads each having an amplification product of the KRAS amplification sample DNA molecule were produced.

<Preparation of Detection Probe Solution>

Single-stranded DNA molecules respectively containing the sequences represented by SEQ ID Nos shown in Table 4 were prepared. The fluorescent substances shown in Table 4 were respectively bound to the single-stranded DNA molecules at the 5'-terminal thereof to prepare detection probes each labeled with a fluorescent substance. The common probe could hybridize with both of amplification products of the wild-type human KRAS gene and the mutant human KRAS gene which can be amplified with the primer set shown in Table 1, and the sequence represented by SEQ ID NO: 5 contained a complementary sequence to a sequence common in the amplification products (see the sequence parts enclosed in boxes in the sequences shown in Table 2). The Wt detection probe could hybridize with an amplification product of the wild-type human KRAS gene which can be amplified with the primer set shown in Table 1, and the sequence represented by SEQ ID NO: 6 contained a complementary sequence to the Wt detection sequence. The Mut detection probe could hybridize with an amplification product of the mutant human KRAS gene which can be amplified with the primer set, and the sequence represented by SEQ ID NO: 7 contained a complementary sequence to the Mut detection sequence.

TABLE 4

| Name of probe | SEQ ID NO: | Sequence 5'→3' | Fluorescent substance |
|---|---|---|---|
| Common probe | SEQ ID NO: 5 | TGACGATACAGCTAATTCA | Cy3 |
| Wt detection probe | SEQ ID NO: 6 | TGCTGGTGGCGTAGGC | FAM |
| Mut detection probe | SEQ ID NO: 7 | TGCTGGTGACGTAGGC | Cy5 |

Each of the three-types of detection probes thus prepared was added to a hybridization solution in such a manner that the final concentration of each probe became 0.1 mol/L. In this manner, detection probe solutions were prepared (the total probe concentration: 0.3 mol/L).

<Collection of Magnetic Beads and Hybridization with Detection Probe>

Each of the emulsions containing the magnetic beads to each of which the amplified nucleic acid synthesized by the PCR reaction was bound was disrupted with a Breaking buffer (10 mmol/L Tris-HCl pH 7.5, 1%, Triton X-100, 1% sodium dodecyl sulfate, 100 mmol/L sodium chloride, 1 mmol/L ethylenediaminetetraacetic acid), and then the magnetic beads were collected from the solution. The collected magnetic beads were treated with 0.1 mol/L sodium hydroxide, and then washed.

The washed magnetic beads were suspended in the detection probe solution. The resultant suspension was treated at 50° C. for 15 minutes to cause the hybridization between the amplified nucleic acid on the magnetic beads and the detection probe. Subsequently, the magnetic beads were washed with TK buffer (20 mmol/L Tris-HCl pH 8.4, 50 mmol/L potassium chloride) and then suspended in TK buffer.

<Flow Cytometric Analysis>

The magnetic beads in the suspension were measured with BD Accuri C6 flow cytometer (Beckton Dickinson). In this Example, signals (forward scattered light and measurement scattered light) coming from the magnetic beads were obtained by the measurement with a flow cytometer (FCM), and signals (fluorescence originated from the detection probe and fluorescence originated from the common probe) originated from the amplified nucleic acid were also obtained. In this Example, fluorescence originated from the (Cy3-labeled) common probe was received by an FL2 channel in the flow cytometer, fluorescence originated from the (FAM-labeled) Wt detection probe was received by a FL1 channel in the flow cytometer, and fluorescence originated from the (Cy5-labeled) Mut detection probe was received by a FL4 channel in the flow cytometer.

Measurement data that reflected non-aggregative magnetic beads was selected on the basis of the obtained forward scattering and side scattering. It was confirmed that the non-aggregative magnetic beads were magnetic beads to each of which an amplification product of the KRAS amplification sample DNA molecule was bound, on the basis of the fluorescent signal originated from the (Cy3-labeled) common probe (LF2 channel). It was possible to remove autofluorescence originated from the magnetic beads by utilizing a fact that the quality control polynucleotide used in this Example did not contain a region with which the common probe was able to hybridize but contained the detection sequence in number several times more than the KRAS amplification sample DNA molecule. For example, the number of (FAM-labeled) Wt detection probes which could bind to magnetic beads to each of which an amplification product of the quality control polynucleotide (Wt, n=5) was bound is theoretically five times larger than the number of (FAM-labeled) Wt detection probes which could bind to magnetic beads to each of which an amplification product of the KRAS amplification sample DNA was bound, as mentioned below. As a result, a FAM-originated fluorescent signal having a several times larger intensity was obtained from each of the magnetic beads to each of which an amplification product of the quality control polynucleotide (Wt, n=5) was bound. Due to this larger intensity of the FAM-originated fluorescent signal, leakage into the LF2 channel occurred. By utilizing the leakage of the FAM-originated fluorescent signal into the LF2 channel, it was confirmed that the magnetic beads were magnetic beads to each of which an amplification product of the quality control polynucleotide (Wt, n=5) was bound.

In the case where autofluorescence originated from the magnetic beads is present, the autofluorescence can be removed using the common probe and therefore the analysis of the KRAS amplification sample DNA can be performed with higher accuracy. In the case where autofluorescence originated from the magnetic beads is present, the autofluorescence can also be removed by utilizing a fact that the total number of detection sequences and sequences complementary to the detection sequences in the quality control polynucleotide is different from the total number of detection sequences and sequences complementary to the detection sequences in the amplification product of the target nucleic acid.

Figure 5A:
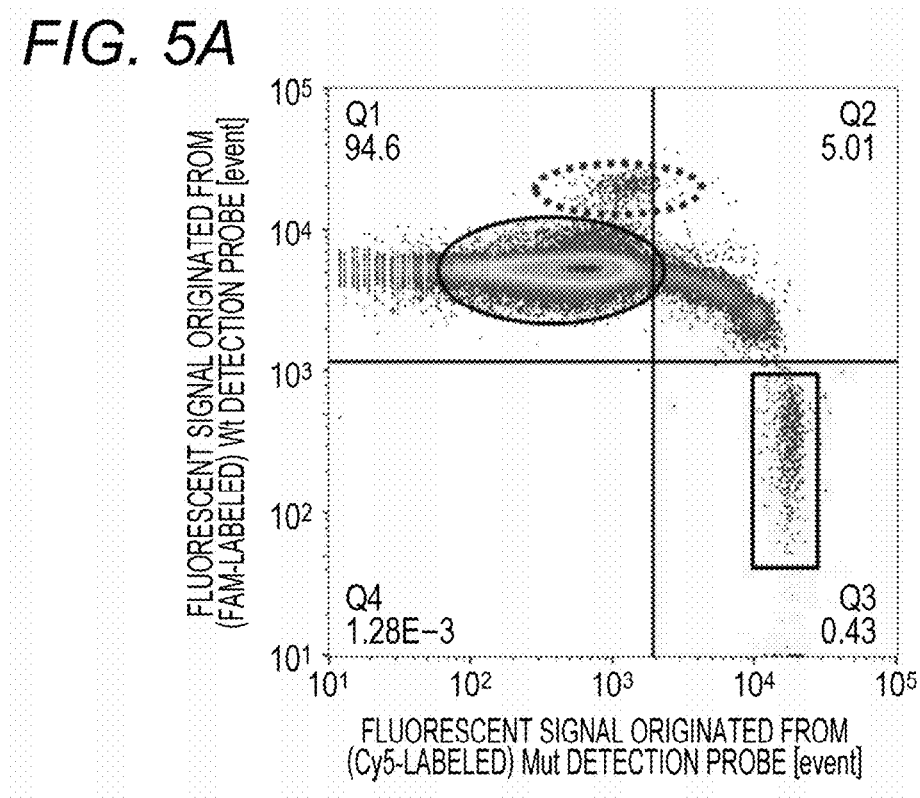
FIGS. 5A and 5B show schematic diagrams illustrating 2D scattergrams which show the results of an illustrative method for quality control in the nucleic acid amplification of human KRAS gene. In the 2D scattergram shown in FIG. 5A, a quality control polynucleotide (Wt, n=5) is present (+). In the 2D scattergram shown in FIG. 5B, the quality control polynucleotide (Wt, n=5) is absent (−). In each of FIGS. 5A and 5B, a signal that reflects an amplification product of a mutant (Mut) KRAS gene is assigned to x-axis and a signal that reflects an amplification product of a wild-type (Wt) KRAS gene is assigned to y-axis.

For the selected measurement data, a 2D scattergram was produced, in which the intensity of a fluorescent signal originated from the Mut detection probe was assigned to x-axis and the intensity of a fluorescent signal originated from the Wt detection probe was assigned to y-axis (FIG. 5A). In the 2D scattergram, the number of dots in an area corresponding to magnetic beads that emitted fluorescence originated from the Wt detection probe (wherein the number of dots corresponds to the number of magnetic beads that indicate the presence of the wild-type KRAS gene) and the number of dots in an area corresponding to magnetic beads that emitted fluorescence originated from Mut detection probe (wherein the number of dots corresponds to the number of magnetic beads that indicate the presence of the mutant KRAS gene) were counted separately. In FIG. 5A, the 2D scattergram was divided into four areas (Q1 to Q4), and the ratio (%) of the number of dots in each of the counted areas to the total number of dots in the 2D scattergram was displayed in the areas. In the Examples mentioned below, the ratio of dots was also displayed in each of the areas (Q1 to Q4) in the 2D scattergram in the same manner.

Comparative Example 1

Figure 5B:
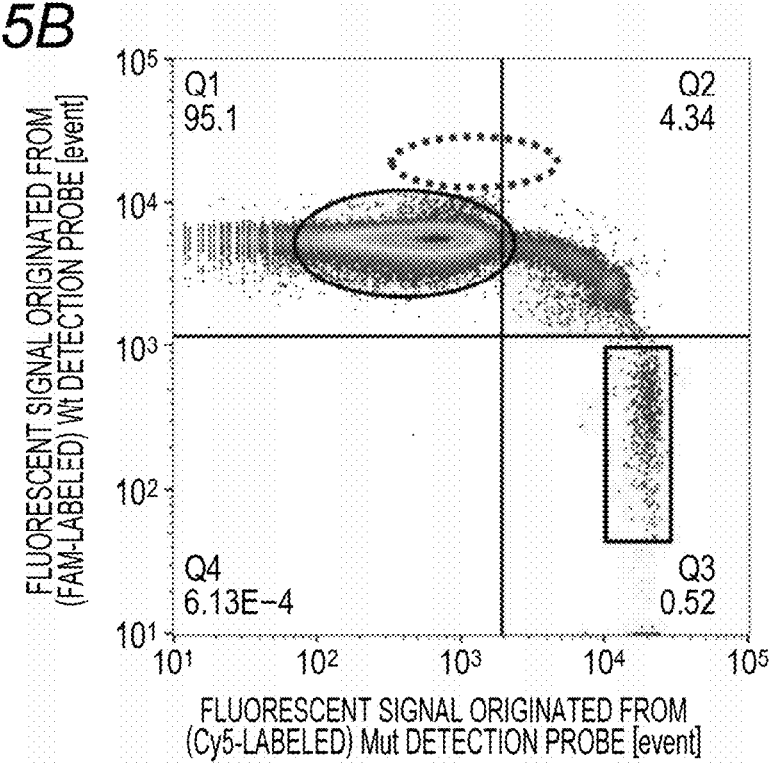

In Comparative Example 1, the BEAMing method, the collection of magnetic beads, the hybridization and the flow cytometry (FCM) analysis were carried out in substantially the same manner as in Example 1, except that a PCR reaction solution that did not contain the quality control polynucleotide (Wt, n=5) was prepared (FIG. 5B).

In FIG. 5A which shows the result of Example 1 (in which the quality control polynucleotide (Wt, n=5) was contained, (+)), many dots were observed in an area located between the y-axis values of $3 \times 10^3$ and $1 \times 10^4$ [event] (i.e., an area enclosed in a solid-line circle). In FIG. 5B which shows the result of Comparative Example 1 (in which the quality control polynucleotide (Wt, n=5) was not contained, (−)), many dots were also observed in an area located between the y-axis values of $3 \times 10^3$ and $1 \times 10^4$ [event] (i.e., an area enclosed in a solid-line circle). The clusters of dots in these areas indicate that the intensities of fluorescent signals originated from the (FAM-labeled) Wt detection probe are relatively strong and the intensities of fluorescent signals originated from the (Cy5-labeled) Mut detection probe are relatively weak. Consequently, it is suggested that the magnetic beads corresponding to the dots in this area reflect the presence of wild-type KRAS gene in the DNA sample. The ratio of the number of dots in this area to the total number of dots in the 2D scattergram (i.e., ([the number of dots in this area]/[the total number of dots]×100) can be calculated. This ratio can reflect the content of wild-type KRAS gene in the tested DNA sample. In Example 1, an amplification product of a DNA sample in which a plasmid carrying the gene sequence for wild-type human KRAS and a plasmid carrying the gene sequence for mutant human KRAS c.38G>A were mixed at a mixing ratio of 99:1 was used.

In each of the 2D scattergrams shown in FIGS. 5A and 5B, a cluster of dots was observed in an area located between the x-axis value of $1 \times 10^4$ and $3 \times 10^4$ (i.e., an area enclosed in a solid-line box). The clusters of dots in this area indicates that the intensities of fluorescent signals originated from the (Cy5-labeled) Mut detection probe are relatively strong and the intensities of fluorescent signals originated from the (FAM-labeled) Wt detection probe are relatively weak. Consequently, it is suggested that the magnetic beads corresponding to the dots in this area reflect the presence of a mutant KRAS gene in the DNA sample. As mentioned above, the ratio of the number of dots in this area to the total number of dots in the 2D scattergram can be calculated. The ratio can reflect the content of the mutant KRAS gene in the tested DNA sample.

In FIG. 5A (quality control polynucleotide (Wt, n=5) (+)), a cluster of dots, which can be distinguished from a cluster of dots present in an area located between the y-axis values of $3 \times 10^3$ and $1 \times 10^4$ and enclosed in a solid-line circle, was observed in an area located between the y-axis values of $1 \times 10^4$ and $3 \times 10^4$ (an area enclosed in a solid-line circle). In FIG. 5B (quality control polynucleotide (Mut, n=5) (−)), no dot was observed in an area corresponding to the area enclosed in a broken-line circle in FIG. 5A. The cluster of dots in the area enclosed in the broken-line circle in FIG. 5A demonstrates that the intensities of fluorescent signals originated from the (FAM-labeled) Wt detection probe in the cluster are several times larger than the intensities of fluorescent signals coming from the cluster of dots in the area enclosed in the solid-line circle.

These facts suggest that the number of Wt detection probes which hybridized with the magnetic beads corresponding to the dots in the area enclosed in the broken-line circle in each of FIGS. 5A and 5B is several times larger than the number of Wt detection probes which hybridized with the magnetic beads corresponding to the dots in the area enclosed in the solid-line circle in each of the FIGS. 5A and 5B. Consequently, it is understood that the cluster of dots in the area enclosed in a broken-line circle in FIG. 5A can reflect magnetic beads to each of which an amplification product of the quality control polynucleotide (Wt, n=5) having five detection sequences with which the Wt detection probe can hybridize is bound. It is also understood that the clusters of dots in the area enclosed in the solid-line circle in each of FIGS. 5A and 5B can reflect magnetic beads to each of which an amplification product of wild-type KRAS amplification DNA having one detection sequence with which Wt detection probe can hybridize is bound.

Example 2 and Comparative Example 2

Figure 6A:
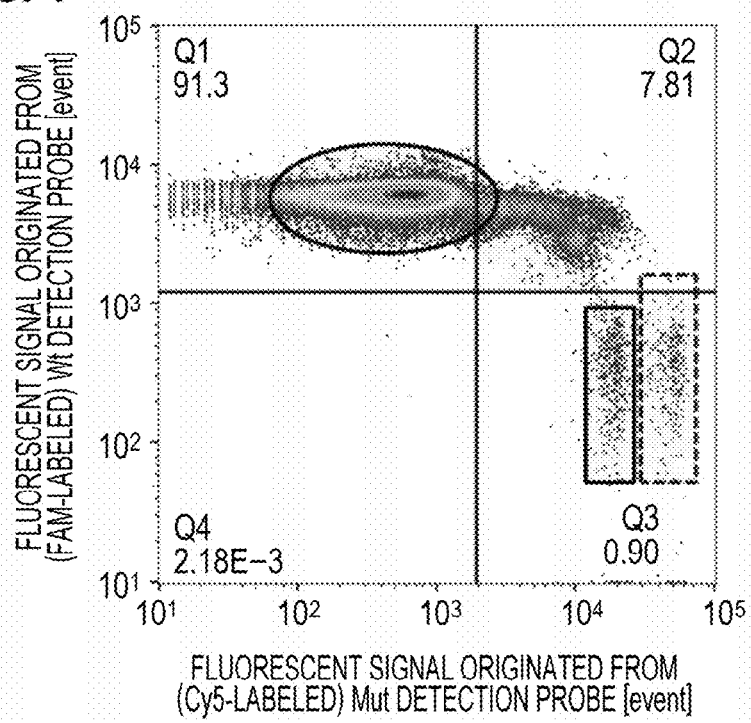
FIGS. 6A and 6B show schematic diagrams illustrating 2D scattergrams.

In Example 2, the BEAMing method, the collection of magnetic beads, the hybridization and the FCM analysis were carried out in substantially the same manner as in Example 1, except that a PCR reaction solution was prepared using the quality control polynucleotide (Mut, n=5) in place of the quality control polynucleotide (Wt, n=5) (FIG. 6A).

Figure 6B:
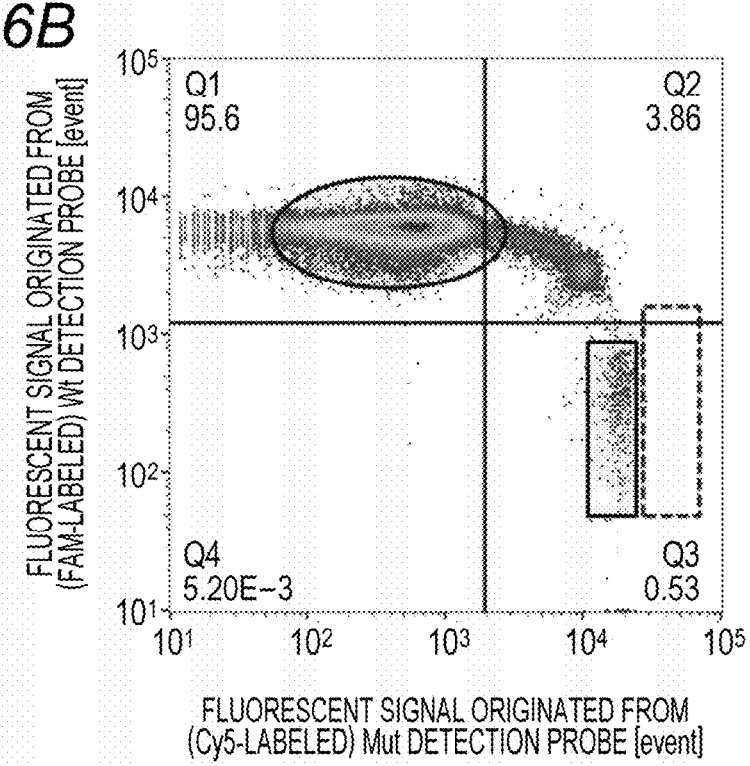

In Comparative Example 2, the BEAMing method, the collection of magnetic beads, the hybridization and the FCM analysis were carried out in substantially the same manner as in Example 2, except that a PCR reaction solution that did not contain the quality control polynucleotide (Mut, n=5) was prepared (FIG. 6B).

The results of Example 2 and Comparative Example 2 are as follows: like the results of Example 1 and Comparative Example 1, many dots were observed in an area that reflected the presence of wild-type KRAS gene in the DNA sample (FIGS. 6A and 6B, areas each enclosed in a solid-line circle), and a cluster of dots was observed in an area that reflected the presence of mutant KRAS gene (FIGS. 6A and 6B, areas each enclosed in a solid-line box).

In FIG. 6A (quality control polynucleotide (Mut, n=5) (+)), a cluster of dots, which can be distinguished from a cluster of dots present in an area that is located between the x-axis values of $1\times10^4$ and $2\times10^4$ and is enclosed in a solid-line box, is observed in an area which is located between the x-axis values of $3\times10^4$ and $6\times10^5$ and is enclosed in a broken-line box. In FIG. 6B (quality control polynucleotide (Mut, n=5) (−)), no dot was observed in an area corresponding to the area enclosed in the broken-line box in FIG. 6A. The cluster of dots in the area enclosed in the broken-line box in FIG. 6A demonstrates that the intensity of a fluorescent signal originated from the (Cy5-labeled) Mut detection probe is several times larger than the intensities of a fluorescent signal coming from the cluster of dots in the area enclosed in the solid-line box.

These facts suggest that the number of Mut detection probes which hybridized with the magnetic beads corresponding to the dots in the area enclosed in the broken-line box in each of FIGS. 6A and 6B is several times larger than the number of Mut detection probes which hybridized with the magnetic beads corresponding to the dots in the area enclosed in the solid box in each of FIGS. 6A and 6B. Therefore, it is understood that the cluster of dots in the area enclosed in the broken-line box in FIG. 6A can reflect the magnetic beads to each of which an amplification product of the quality control polynucleotide (Mut, n=5) having five detection sequences with which the Mut detection probe can hybridize is bound. It is also understood that the cluster of dots in the area enclosed in the solid-line box in each of FIGS. 6A and 6B can reflect the magnetic beads to each of which an amplification product of the mutant KRAS amplification DNA having one detection sequence with which the Mut detection probe can hybridize is bound.

From the results of Example 1 and Example 2, it is understood that it is possible to determine as to whether or not a series of steps including the preparation of a nucleic acid, the preparation of compartments, the amplification of the nucleic acid and the detection of signals are proper by the method for controlling quality of nucleic acid amplification according to one aspect, because a quality control polynucleotide is used, which can be amplified using the same primer set as that used for the amplification of a target nucleic acid and can be detected separately from an amplification product of the target nucleic acid by using the same detection probe as that used for the detection of the amplification product of the target nucleic acid.

From the results of Example 1 and Example 2, it is also understood that the quality control polynucleotide according to one aspect can be used in the method for controlling quality in the detection of a mutant.

[Example 3]<Correlation Between Number of Copies of Quality Control Polynucleotide and Intensity of FCM Detection Signal>

With the PCR reaction solution prepared in Example 1 were spiked 25,000 copies, 50,000 copies, 100,000 copies, 200,000 copies, 400,000 copies and 800,000 copies of the quality control polynucleotide (Wt, n=5), respectively. Subsequently, the BEAMing method, the collection of magnetic beads, the hybridization and the FCM analysis were carried out in substantially the same manner as in Example 1. The data obtained by the FCM analysis was further analyzed using FlowJo software (FlowJo), and an average value of the intensities of fluorescent signals originated from the quality control polynucleotide after the PCR reaction was calculated (FIG. 7A).

Figure 7A:
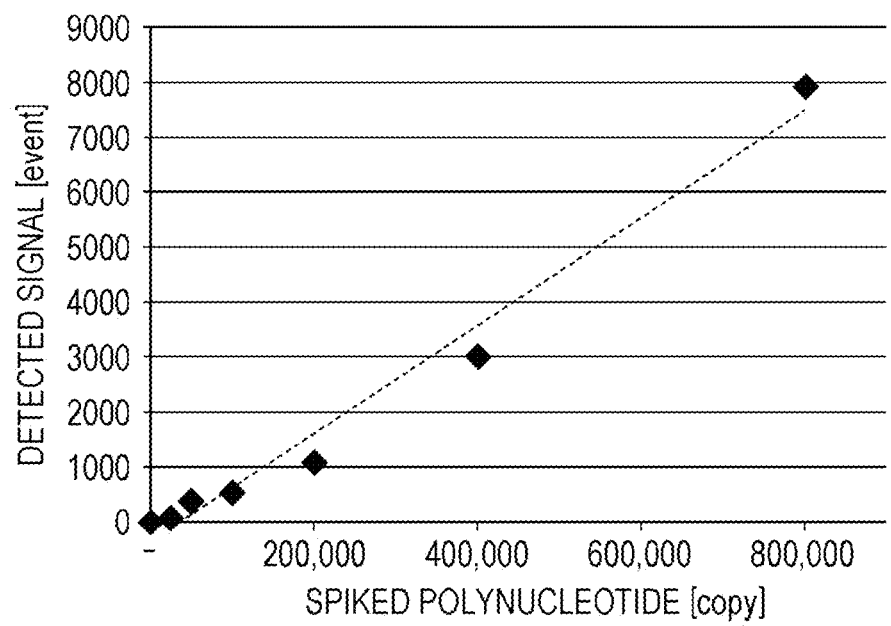
FIGS. 7A and 7B show scatter diagrams each illustrating the correlation between the number of copies of a quality control polynucleotide (FIG. 7A: Wt, n=5, FIG. 7B: Mut, n=5) spiked with a nucleic acid amplification reaction solution and the intensity of a detection signal.

FIG. 7A shows a scatter diagram in which the number of copies of the spiked quality control polynucleotide is assigned to x-axis and the intensity of a fluorescent signal detected in the FCM measurement is assigned to y-axis. The broken line in FIG. 7A is a regression line, and the equation for the regression line is as follows: $y=0.0098x-357$. FIG. 7A demonstrates that the fluorescent signal intensity that can correspond to the quantity of an amplification product of the spiked quality control polynucleotide increases with the increase in number of copies of the spiked quality control polynucleotide.

Similarly, with the PCR reaction solution prepared in Example 2 were spiked 25,000 copies, 50,000 copies, 100,000 copies, 200,000 copies, 400,000 copies and 800,000 copies of the quality control polynucleotide (Mut, n=5), respectively. Subsequently, the BEAMing method, the collection of magnetic beads, the hybridization and the FCM analysis were carried out in substantially the same manner as in Example 2. The data obtained by the FCM analysis was further analyzed using FlowJo software (FlowJo), and an average value of the intensities of fluorescent signals originated from the quality control polynucleotide after the PCR reaction was calculated (FIG. 7B).

Figure 7B:
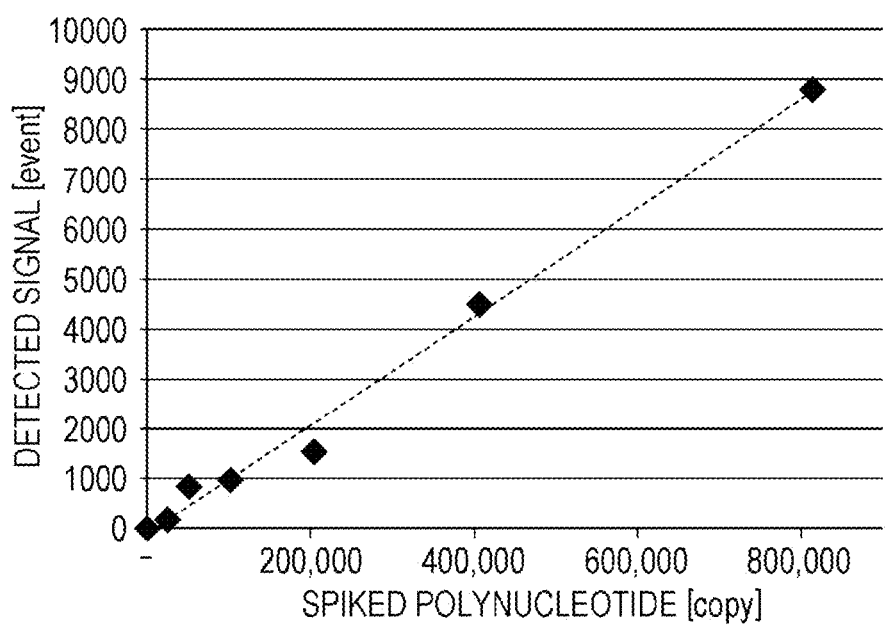

FIG. 7B shows a scatter diagram in which the number of copies of the spiked quality control polynucleotide is assigned to x-axis and the intensity of a fluorescent signal detected in the FCM measurement is assigned to y-axis. The broken line in FIG. 7B is a regression line, and the equation for the regression line is as follows: $y=0.011x-68$. FIG. 7B also demonstrates that the fluorescent signal intensity that can correspond to the quantity of an amplification product of the spiked quality control polynucleotide increases with the increase in number of copies of the spiked quality control polynucleotide.

As illustrated in FIGS. 7A and 7B, there is a positive correlation between the number of copies of the spiked quality control polynucleotide and the intensity of a fluorescent signal detected by FCM. This result demonstrates the quantitativity of the nucleic acid amplification quality control method using the quality control polynucleotide which is disclosed in the present disclosure.

[Example 4]<Correlation Between Number of Detection Sequences in Quality Control Polynucleotide and Intensity of FCM Detection Signal>

PCR reaction solutions respectively containing 40,000 copies of the quality control polynucleotides (Wt, n=5), (Wt, n=4), (Wt, n=3) and (Wt, n=2) and a PCR reaction solution containing no quality control polynucleotide (wherein the number (n) of the Wt detection sequence in wild-type human KRAS gene=1) were prepared, and then the BEAMing method, the collection of magnetic beads, the hybridization and the FCM analysis were carried out in substantially the same manner as in Example 1. The date obtained by the FCM analysis was further analyzed using FlowJo software, and an average value and a standard deviation (SD) of the intensities of fluorescent signals originated from the quality control polynucleotide after the PCR reaction were calculated (FIG. 8).

Figure 8:
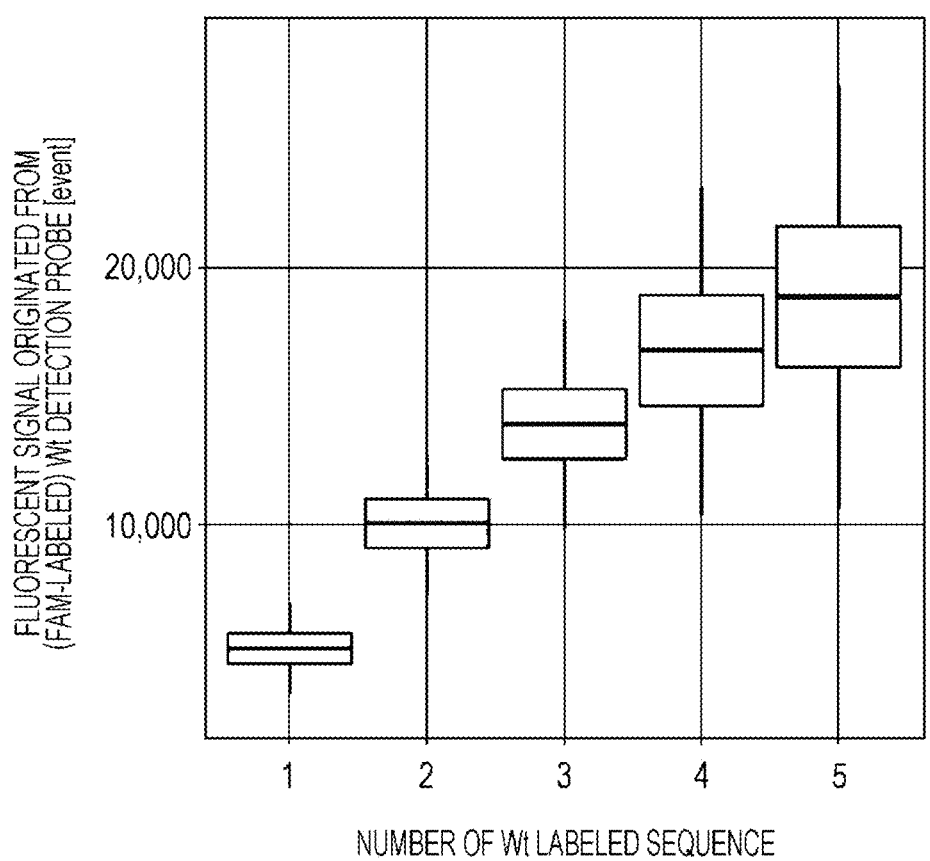
FIG. 8 shows a box plot illustrating the correlation between the number of detection sequences in a quality control polynucleotide and the intensity of a detection signal.

FIG. 8 shows a box plot in which the number of Wt detection sequences is assigned to x-axis and the intensity of a fluorescent signal originated from the (FAM-labeled) Wt detection probe is assigned to y-axis. In the box plot, each end of each box shows a value "average value ±1SD" and each end of each whisker shows a value "average value ±3SD".

As illustrated in FIG. 8, it is understood that there is a positive correlation between the fluorescent signal intensity that can correspond to the number of detection sequences in the amplified quality control polynucleotide and the number of detection sequences in the quality control polynucleotide.

In Example 4, as the criterion on the basis of which the target nucleic acid and the quality control polynucleotide can be distinguished from each other, the results shown in FIG. 8 are referred, provided that the values of the average value ±1SD of the intensities of the fluorescent signals do not overlap each other. When it is hypothesized that one (n=1) detection sequence is present in the target nucleic acid, if at least two (n≥2) detection sequences are present in the quality control polynucleotide, it is suggested that the target nucleic acid and the quality control polynucleotide can be detected separately by using one type of detection probe. On the basis of the same criterion, it is understood that, when it is hypothesized that two (n=2) detection sequences are present in the target nucleic acid for example, it is required for the quality control polynucleotide to contain one (n=1) detection sequence or, alternatively, to contain at least three (n≥3) detection sequences, for the purpose of distinguishing the target nucleic acid and the quality control polynucleotide from each other.

According to Example 4, it is understood that, when a quality control polynucleotide in which the total number of detection sequences and sequences complementary to the detection sequences is different from the total number of detection sequences and sequences complementary to the detection sequences which can be present in the target nucleic acid is used in the nucleic acid amplification quality control method using the quality control polynucleotide according to one aspect, it becomes possible to detect the target nucleic acid and the quality control polynucleotide separately by using only one type of detection probe.

Example 5 and Comparative Example 3

Figure 9A:
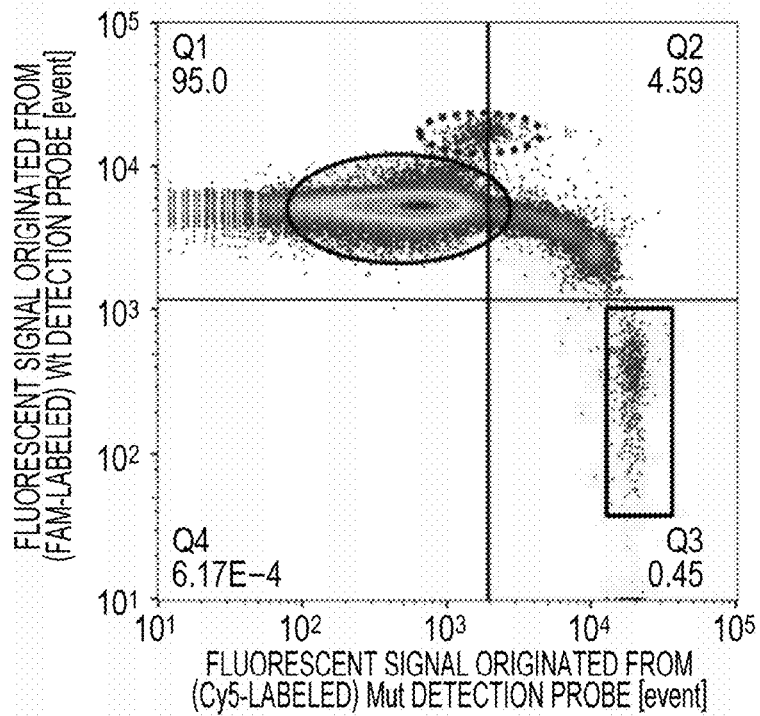
FIGS. 9A and 9B show schematic diagrams illustrating 2D scattergrams.

In Example 5, the BEAMing method, the collection of magnetic beads, the hybridization and the FCM analysis were carried out in substantially the same manner as in Example 1, except that 50,000 copies of a quality control polynucleotide (Wt, n=6) were spiked, in place of 100,000 copies of a quality control polynucleotide (Wt, n=5), with the PCR reaction solution prepared in Example 1 (FIG. 9A). In Comparative Example 3, the BEAMing method, the collection of magnetic beads, the hybridization and the FCM analysis were carried out in substantially the same manner as in Example 5, except that a PCR reaction solution which did not contain the quality control polynucleotide (Wt, n=6) was prepared (FIG. 9B).

In FIG. 9A (quality control polynucleotide (Wt, n=6) (+)), a cluster of dots, which can be distinguished from many dots present in an area enclosed in a solid-line circle located between the y-axis values of about $3 \times 10^3$ and about $1 \times 10^4$, was observed in an area enclosed in a broken-line circle located between the y-axis values of about $1.5 \times 10^4$ and about $3 \times 10^4$. In FIG. 9B (quality control polynucleotide (Wt, n=6) (−)), no dot was observed in an area corresponding to the area enclosed in the broken-line circle in FIG. 9A. The cluster of dots in the area enclosed in the broken-line circle in FIG. 9A demonstrates that the intensities of fluorescent signals originated from the (FAM-labeled) Wt detection probe are several times larger than those of fluorescent signals coming from the cluster of dots in the area enclosed in the solid-line circle.

Figure 9B:
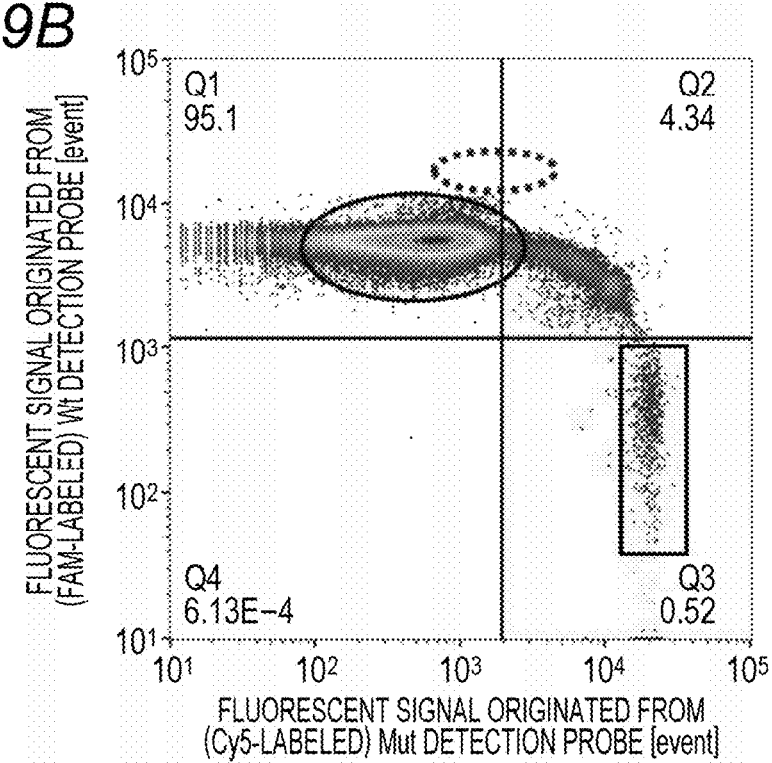

These facts suggest that the number of Wt detection probes which hybridized with the magnetic beads corresponding to the dots present in the area enclosed in the broken-line circle in each of FIGS. 9A and 9B is several times larger than the number of Wt detection probes which hybridized with the magnetic beads corresponding to the dots present in the area enclosed in the solid-line circle in each of FIGS. 9A and 9B. It is understood that the cluster of dots present in the area enclosed in the broken-line circle in FIG. 9A can reflect the magnetic beads to each of which an amplification product of the quality control polynucleotide (Wt, n=6) having six detection sequences with which the Wt detection probe can hybridize is bound. It is also understood that the cluster of dots present in the solid-line circle in each of FIGS. 9A and 9B can reflect the magnetic beads to each of which an amplification product of wild-type KRAS amplification DNA having one detection sequence with which the Wt detection probe can hybridize is bound.

In the control polynucleotide (Wt, n=6) used in Example 5, a spacer sequence located between the Wt detection sequences had a length of 2 bp (see Table 3, the number of nucleotides between the underlined detection sequences (chain length) in the sequence represented by SEQ ID NO: 15). In each of the control polynucleotides (Wt, n=5), (Wt, n=4), (Wt, n=3), (Wt, n=2) and (Mut, n=5) used in Examples 1 to 4, a spacer sequence located between the detection sequences had a length of 5 bp (see Table 3, the chain length between the underlined detection sequences of the sequences respectively represented by SEQ ID NOs: 10 to 14). From the results of Example 5, it is understood that, according to the nucleic acid amplification quality control method using the quality control polynucleotide according to one embodiment, it is possible to detect an amplification product of the quality control polynucleotide and an amplification product of the target nucleic acid separately even when a spacer sequence located between the detection sequences or sequences complementary to the detection sequences has a length of 2 bp.

The invention claimed is:

1. A quality-controlled nucleic acid amplification method, wherein said method comprises the steps of:
preparing a nucleic acid sample containing a target nucleic acid and a quality control polynucleotide;
preparing a compartment containing one molecule of the target nucleic acid and a different compartment containing one molecule of the quality control polynucleotide;
carrying out nucleic acid amplification of the target nucleic acid and the quality control polynucleotide, in the compartments, to produce amplification products;
allowing a detection probe to hybridize to the amplification products, wherein the detection probe produces a detectable signal; and
detecting signal intensities from detection probe that is hybridized to amplification products, wherein the signal intensity from detection probe that is hybridized to an amplification product of the target nucleic acid is distinguishable from the signal intensity from detection probe that is hybridized to an amplification product of the quality control polynucleotide,
wherein the target nucleic acid contains a detection sequence,
and the quality control polynucleotide is
(1) a single-stranded polynucleotide which contains a first region, a second region and a third region, wherein the first region contains a sequence to which a first primer for target nucleic acid amplification can bind, the second region contains a sequence complementary to a sequence to which a second primer for target nucleic acid amplification can bind, and the third region contains either the detection sequence, a sequence complementary to the detection sequence, or both,
(2) a single-stranded polynucleotide which contains a sequence entirely complementary to the sequence recited in item (1), or
(3) a double-stranded polynucleotide which contains both the polynucleotide recited in item (1) and the polynucleotide recited in item (2), wherein the detection probe contains a sequence complementary to the detection sequence, and wherein the sum of the number of copies of the detection sequence and the number of copies of the complementary sequence to the detection sequence in the quality control polynucleotide recited in item (1) is a different integer from the number of copies of the detection sequence in the target nucleic acid.

2. The method according to claim 1, wherein each of the compartments additionally contains the first primer, the second primer, dNTPs and a polymerase.

3. The method according to claim 2,
wherein
the nucleic acid sample contains beads, and
either the first primer, the second primer, or both, are bound to said beads.

4. The method according to claim 3, wherein the compartments contain the beads at a proportion of one bead per compartment.

5. The method according to claim 3, further comprising evaluating the number of beads each containing an amplification product of the quality control polynucleotide, by counting the number of beads that each generate a signal intensity equal to or greater than a predetermined threshold value for the signal intensity.

6. The method according to claim 1, wherein the quality control polynucleotide comprises DNA, RNA or a polynucleotide derivative.

7. The method according to claim 1, wherein the quality control polynucleotide is double-stranded.

8. The method according to claim 1, wherein the third region is located between the first region and the second region in the quality control polynucleotide.

9. The method according to claim 1, wherein
the quality control polynucleotide contains a first spacer sequence upstream from the third region and a second spacer sequence downstream from the third region,
the first spacer sequence and the second spacer sequence are different from each other, and
the first spacer sequence and the second spacer sequence are not complementary to each other.

10. The method according to claim 1, wherein the total number of the detection sequence and complementary sequence to the detection sequence in the quality control polynucleotide is larger than the number of detection sequence in the target nucleic acid.

11. The method according to claim 1, wherein the detection probe is an oligonucleotide labelled with at least one labeling substance selected from the group consisting of a fluorescent substance, an enzyme and a hapten.

12. The method according to claim 11,
wherein
the nucleic acid amplification is carried out in the presence of a polymerase with an exonuclease activity,
the detection probe is an oligonucleotide labeled with a fluorescent substance and a quencher substance, in which the quencher substance is located in the detection probe in such a manner that fluorescence from the fluorescent substance can be quenched, and
the detection probe hybridizes with the target nucleic acid and quality control polynucleotide during the nucleic acid amplification, and the hybridized detection probe is digested by the exonuclease activity of said polymerase so that the fluorescent substance can be separated from the quencher substance to emit a fluorescent signal.

13. The method according to claim 1, wherein the signal produced by the detection probe is a fluorescent signal intensity coming from each of the compartments in the signal detection step.

14. The method according to claim 13, further comprising evaluating the number of compartments each containing an amplification product of the quality control polynucleotide, by counting the number of compartments that each generate a fluorescent signal intensity equal to or larger than a predetermined threshold value for the fluorescent signal intensity.

15. The method according to claim 1, wherein a flow cytometer is used in the signal detection step.

16. The method of claim 1, wherein the target nucleic acid and the quality control polynucleotide are digitally detected.

17. A quality-controlled nucleic acid amplification method that detects a mutation in a target nucleic acid, wherein said method comprises the steps of:
preparing a nucleic acid sample containing a target nucleic acid and a quality control polynucleotide, wherein said target nucleic acid contains a mutation;
preparing a compartment containing one molecule of the target nucleic acid and a different compartment containing one molecule of the quality control polynucleotide; and
carrying out nucleic acid amplification of the target nucleic acid and the quality control polynucleotide, in the compartments, to produce amplification products;
allowing a detection probe to hybridize to the amplification products, wherein the detection probe produces a detectable signal; and
detecting signal intensities from detection probe that is hybridized to amplification products, wherein the signal intensity from detection probe that is hybridized to an amplification product of the target nucleic acid is distinguishable from the signal intensity from detection probe that is hybridized to the amplification product of the quality control polynucleotide,
wherein the target nucleic acid contains a detection sequence,
and the quality control polynucleotide is
(1) a single-stranded polynucleotide which contains a first region, a second region and a third region, wherein the first region contains a sequence to which a first primer for target nucleic acid amplification can bind, the second region contains a sequence complementary to a sequence to which a second primer for target nucleic acid amplification can bind, and the third region contains either the detection sequence, a sequence complementary to the detection sequence, or both,
(2) a single-stranded polynucleotide which contains a sequence entirely complementary to the sequence recited in item (1), or
(3) a double-stranded polynucleotide which contains both the polynucleotide recited in item (1) and the polynucleotide recited in item (2),
and wherein the sum of the number of copies of the detection sequence and the number of copies of the complementary sequence to the detection sequence in the quality control polynucleotide recited in item (1) is a different integer from the number of copies of the detection sequence in the target nucleic acid.

18. The method according to claim 17, wherein the total number of the detection sequence and complementary sequence to the detection sequence in the quality control sequence is larger than the number of detection sequence in the target nucleic acid.

19. The method according to claim 18,
wherein
the nucleic acid sample contains beads,
either the first primer, the second primer, or both, are bound to said beads,
the compartments contain the beads at a proportion of one bead per compartment,
the detection probe hybridizes to amplification products present on the beads, and wherein said method further comprises evaluating the number of beads each containing an amplification product of the quality control polynucleotide, by counting the number of beads that each generate a signal intensity greater than a signal intensity from a bead containing an amplification product of the target nucleic acid.

* * * * *